(12) United States Patent
Suzuki et al.

(10) Patent No.: US 10,990,179 B2
(45) Date of Patent: Apr. 27, 2021

(54) HAPTIC PRESENTATION APPARATUS

(71) Applicant: SONY CORPORATION, Tokyo (JP)

(72) Inventors: Hiroyuki Suzuki, Tokyo (JP); Ryuta Horie, Saitama (JP); Kenichiro Nagasaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/333,274

(22) PCT Filed: Sep. 6, 2017

(86) PCT No.: PCT/JP2017/032129
§ 371 (c)(1),
(2) Date: Mar. 14, 2019

(87) PCT Pub. No.: WO2018/061683
PCT Pub. Date: Apr. 5, 2018

(65) Prior Publication Data
US 2019/0258316 A1 Aug. 22, 2019

(30) Foreign Application Priority Data
Sep. 30, 2016 (JP) .............................. JP2016-192743

(51) Int. Cl.
*G06F 3/01* (2006.01)
*A61B 34/35* (2016.01)
(Continued)

(52) U.S. Cl.
CPC .............. *G06F 3/016* (2013.01); *A61B 34/35* (2016.02); *A61B 34/74* (2016.02); *A61B 34/75* (2016.02);
(Continued)

(58) Field of Classification Search
CPC . G06F 3/016; G06F 3/01; A61B 34/35; A61B 34/74; A61B 34/75; A61B 34/76; B25J 13/00
See application file for complete search history.

(56) References Cited

U.S. PATENT DOCUMENTS 6,184,868 B1   2/2001   Shahoian et al.
8,716,973 B1   5/2014   Lammertse
(Continued)

FOREIGN PATENT DOCUMENTS

EP   2 870 985 A2   5/2015
JP   4-275887 A   10/1992
(Continued)

OTHER PUBLICATIONS

International Search Report dated Nov. 21, 2017 in PCT/JP2017/032129, 2 pages.
(Continued)

*Primary Examiner* — Amine Benlagsir
(74) *Attorney, Agent, or Firm* — Xsensus LLP

(57) ABSTRACT

A haptic presentation apparatus that includes a force sensor that detects force input to an operation portion that is operated by a user, and generates an electric signal corresponding to the detected force, a vibration actuator that presents tactile sensation to the user, a vibration damping member to be interposed between the force sensor and the vibration actuator; a first mechanical part contacting the force sensor; and a second mechanical part contacting the vibration actuator, and the vibration damping member is provided between the first mechanical part and the second mechanical part, such that the vibration damping member contact neither the force sensor nor the vibration actuator.

17 Claims, 18 Drawing Sheets

(51) Int. Cl.
*A61B 34/00* (2016.01)
*B25J 3/00* (2006.01)

(52) U.S. Cl.
CPC ............... *A61B 34/76* (2016.02); *B25J 3/00* (2013.01); *G06F 3/01* (2013.01)

(56) References Cited

U.S. PATENT DOCUMENTS

| | | | |
|---|---|---|---|
| 2010/0312129 A1* | 12/2010 | Schecter | A61B 5/0031 600/508 |
| 2011/0115754 A1 | 5/2011 | Cruz-Hernandez | |
| 2012/0209303 A1* | 8/2012 | Frankhouser | A61B 10/025 606/169 |
| 2013/0041368 A1* | 2/2013 | Cunningham | A61B 18/14 606/34 |
| 2015/0133221 A1 | 5/2015 | Danny | |
| 2015/0153857 A1 | 6/2015 | Aubry et al. | |
| 2015/0209117 A1* | 7/2015 | Flexman | A61B 34/20 600/424 |
| 2015/0357132 A1 | 12/2015 | Ishikawa et al. | |
| 2017/0333146 A1* | 11/2017 | Kerdok | A61B 34/75 |
| 2018/0283487 A1* | 10/2018 | Hattori | G02B 23/16 |

FOREIGN PATENT DOCUMENTS

| | | |
|---|---|---|
| JP | 8-254472 A | 10/1996 |
| JP | 2003-28647 A | 1/2003 |
| JP | 2014-194718 A | 10/2014 |
| JP | 2015-95261 A | 5/2015 |
| JP | 2015-531902 A | 11/2015 |
| JP | 2015-230620 A | 12/2015 |

OTHER PUBLICATIONS

Extended European Search Report dated Aug. 22, 2019, issued in corresponding European Patent Application No. 17855641.1.

\* cited by examiner

HAPTIC PRESENTATION APPARATUS

TECHNICAL FIELD

The present disclosure relates to a haptic presentation apparatus.

BACKGROUND ART

In recent years, as medical robot systems used when endoscopic surgery is carried out, master-slave medical robot systems have been known that make it possible to approach affected sites without making large incisions on the bodies of patients. In such a medical robot system, a surgeon (user) such as a doctor operates a master apparatus including an input interface, and a slave apparatus including a medical instrument such as forceps or tweezers is remotely operated in accordance with the operation of the surgeon. The slave apparatus is configured, for example, as an arm robot with a surgical instrument held on the front end, and can change the position or attitude of the surgical instrument in the abdomen with a high degree of freedom and a wide movable area. In the medical robot system, in the case where force generated in a slave apparatus is not transmitted to a surgeon, the surgeon can fail to adjust the moving operation amount or force, and damage living tissue of a patient.

Then, medical robot systems have been known that adopt bilateral control which present force generated in slave apparatuses to master apparatuses. In bilateral control, feedback control is performed such that the positions and force of surgical instruments and input interfaces agree with each other between a slave apparatus and a master apparatus. A medical robot system that adopts the bilateral control includes an apparatus configured to present haptic sensation in accordance with the force of an input operation of a user detected by a force sensor provided to a master apparatus.

For example, Patent Literature 1 discloses a master apparatus including three force sensors that detect the respective force components in the directions of three axes (x, y, and z) orthogonal to each other, three respective angle sensors that detect a roll angle, a pitch angle and a yaw angle, and three position sensors that detect the respective front end positions of a dental tool handle in the xyz coordinate system. The master apparatus is a haptic presentation apparatus including a parallel link structure with a multi-degree of freedom and a force sensor, and drive control over an actuator which controls the attitude of the parallel link structure is performed in accordance with the force of an input operation of a user detected by the force sensor.

In addition, as technology applicable to a medical apparatus, Patent Literature 2 discloses a pressure sensation/tactile sensation presenting apparatus that expresses pseudo pressure sensation/tactile sensation with vibration as an expression of an operation situation. The pressure sensation/tactile sensation presenting apparatus uses a pressure sensation/tactile sensation sensor to detect a situation in which a surgical instrument such as forceps comes into contact with a target object, drives a pressure sensation/tactile sensation presenting device such as a voice coil in accordance with an output of the pressure sensation/tactile sensation sensor, and transmits pressure sensation/tactile sensation to a fingertip of a user.

CITATION LIST

Patent Literature

Patent Literature 1: U.S. Pat. No. 8,716,973B
Patent Literature 2: JP H08-254472A

DISCLOSURE OF INVENTION

Technical Problem

Here, in the case where a pressure sensation/tactile sensation presenting device (vibration actuator) as described in Patent Literature 2 is mounted on a haptic presentation apparatus as described in Patent Literature 1, vibration of the vibration actuator can be transmitted to a force sensor. The vibration of the vibration actuator serves as noise in bilateral control, and is thus likely to bring about unfavorable effects on the bilateral control.

Accordingly, the present disclosure proposes a novel and improved haptic presentation apparatus capable of suppressing the transmission of vibration of a vibration actuator used to present pressure sensation/tactile sensation (which will also be generically referred to as "tactile sensation" below) to a force sensor.

Solution to Problem

According to the present disclosure, there is provided a haptic presentation apparatus including: a force sensor configured to detect force input to an operation portion that is operated by a user; a vibration generating source configured to present haptic sensation or tactile sensation to the user; and a vibration damping member configured to be interposed between the force sensor and the vibration generating source.

Advantageous Effects of Invention

According to the present disclosure as described above, it is possible to suppress the transmission of vibration of a vibration actuator used to present tactile sensation to a force sensor.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
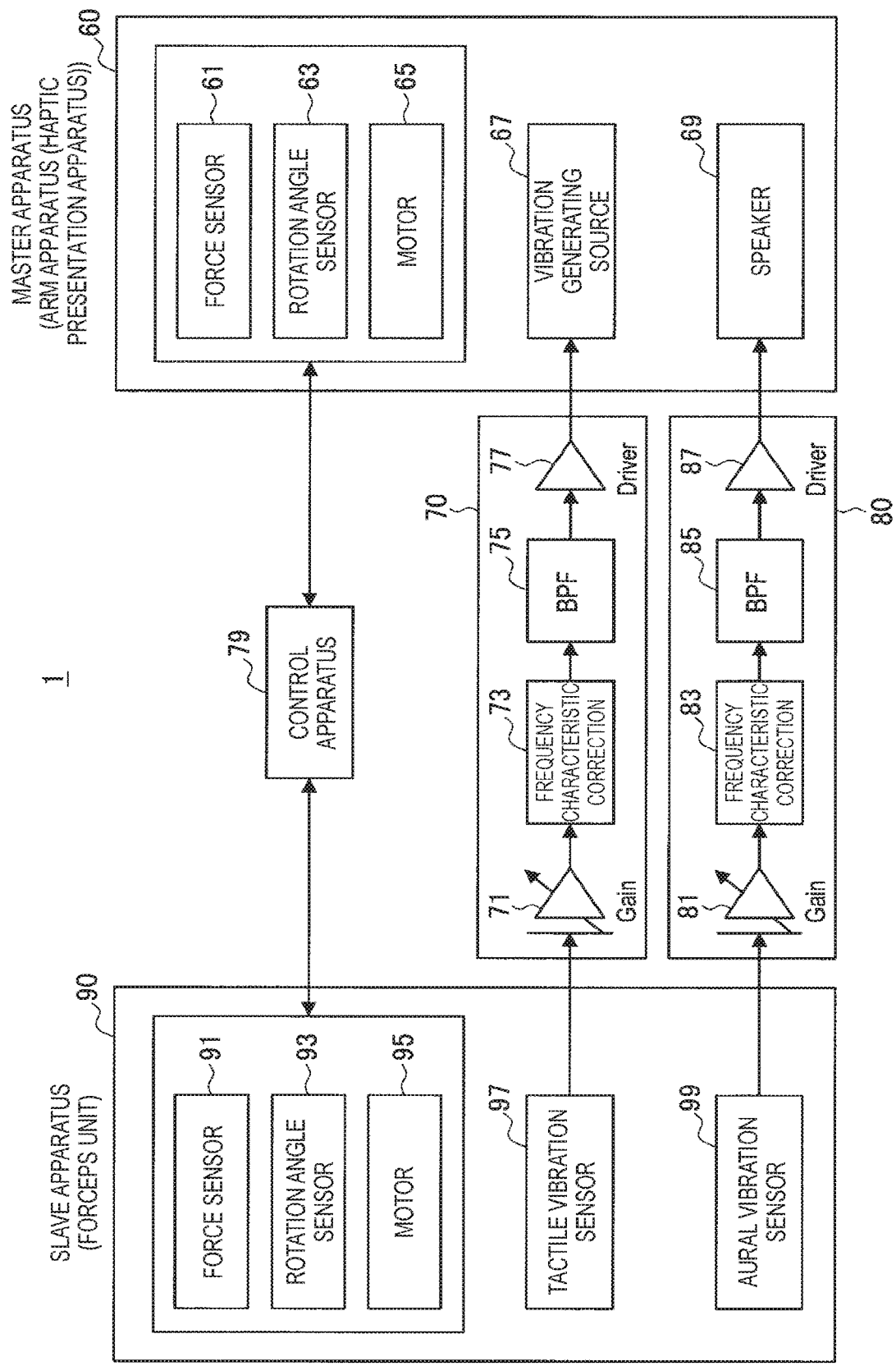
FIG. 1 is an explanatory diagram illustrating a configuration example of a medical robot system to which a haptic presentation apparatus according to an embodiment of the present disclosure is applicable.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Configuration Example of Medical Robot System
2. Overall Configuration Example Haptic Presentation Apparatus (Master Apparatus)
3. Operation Portion
3-1. Overall Configuration Example
3-2. Vibration Transmission Suppressing Structure
3-3. Modification Examples
4. Conclusion 1. Configuration Example of Medical Robot System With reference to FIG. 1, a configuration example of a medical robot system to which a haptic presentation apparatus according to an embodiment of the present disclosure is applicable will be described. A medical robot system 1 illustrated in FIG. 1 is a master-slave medical robot system. In the medical robot system 1, a user operates a master apparatus 60 to transmit an operation command to a slave apparatus 90 through a wired or wireless communication means and remotely operate the slave apparatus 90. The haptic presentation apparatus according to the present embodiment can be applied to the master apparatus 60.

The slave apparatus 90 that is remotely operated may include, for example, an arm with six degrees of freedom, and may be a forceps unit with forceps attached to the front end of the arm. The slave apparatus 90 may include a medical instrument such as tweezers or a cutting instrument instead of forceps. The slave apparatus 90 changes the position or direction of the forceps on the basis of an operation command from the master apparatus 60, and causes the forceps to perform a grasping operation. In addition, the master apparatus 60 may be, for example, an arm apparatus including a grasping-type operation portion that is grasped by a user, and an arm that has the operation portion attached to the front end and has six degrees of freedom. A user displaces the position and attitude of the operation portion of the master apparatus 60 to remotely operate the position and attitude of the forceps of the slave apparatus 90. In addition, a user performs a grasping operation of the operation portion of the master apparatus 60 to remotely operate a grasping operation of the forceps of the slave apparatus 90.

FIG. 1 illustrates that the medical robot system 1 includes the slave apparatus 90, the master apparatus 60, a control apparatus 79, a first vibration transmission portion 70, and a second vibration transmission portion 80. The control apparatus 79 drives the slave apparatus 90 in accordance with an instruction input via the master apparatus 60. The first vibration transmission portion 70 transmits vibration detected by a tactile vibration sensor 97 provided to the slave apparatus 90 to the master apparatus 60. The second vibration transmission portion 80 transmits vibration detected by an aural vibration sensor 99 provided to the slave apparatus 90 to the master apparatus 60.

Note that the block diagram illustrated in FIG. 1 illustrates only components that are necessary in particular to describe the present disclosure. The medical robot system 1 may also include a variety of components included in a general master-slave medical robot system in addition to the illustrated components.

The medical robot system 1 has information transmission systems roughly divided into a system for performing drive control over the slave apparatus 90 and presenting haptic sensation to a surgeon, and a system for transmitting vibration detected on the slave apparatus 90 side to the surgeon. The following simply describes the medical robot system 1 for each of the information transmission systems.

First, the system for performing drive control over the slave apparatus 90 and presenting haptic sensation to a surgeon will be described. In drive control over the slave apparatus 90, a surgeon operates the operation portion attached to the front end of the arm of the master apparatus 60 to transmit information indicating an instruction to drive the arm of the slave apparatus 90 from the master apparatus 60 to the control apparatus 79. In the case where the surgical instrument includes a drivable section like the forceps described above, information indicating an instruction to drive the surgical instrument can also be transmitted together from the master apparatus 60 to the control apparatus 79. In the present embodiment, the master apparatus 60 includes a grasping-type operation portion. The configuration of the operation portion will be described below in detail.

The master apparatus 60 includes a force sensor (torque sensor) 61, a rotation angle sensor 63, and a motor 65 as components for performing drive control over the slave apparatus 90 and presenting haptic sensation. The force sensor 61 is provided, for example, to a connected part between the arm and the operation portion attached to the front end of the arm, and detects force acting in the directions of three axes orthogonal to each other. That is, the force sensor 61 detects force input by a surgeon to the operation portion. In addition, the rotation angle sensors 63 are provided to a plurality of joint portions of the arm, and detect the rotation angles of the respective joint portions. The rotation angle sensor 63 may be, for example, an encoder.

The control apparatus 79 performs a variety of arithmetic operations related to drive control over the slave apparatus 90 on the basis of information input from the force sensor 61 and the rotation angle sensor 63. For example, the control apparatus 79 calculates torque to be generated in each motor 95 of the arm of the slave apparatus 90 on the basis of force acting on the operation portion which is detected by the force sensor 61 in the case where force control is used to perform drive control over the slave apparatus 90. In addition, the control apparatus 79 calculates the target value of the rotation angle of each joint portion of the arm of the slave apparatus 90 on the basis of the rotation angle of each joint portion of the arm which is detected by the rotation angle sensor 63 in the case where position control is used to perform drive control over the slave apparatus 90. In addition, in the case where the surgical instrument of the slave apparatus 90 includes a drivable section, the amount of control for driving the surgical instrument can be calculated by the control apparatus 79.

In the present embodiment, as a scheme of drive control over the slave apparatus 90, a variety of publicly known control systems may be used. As the control apparatus 79, what is adapted to an adopted control system can be constructed as appropriate. The specific configuration of the control apparatus 79 may be similar to existing configurations corresponding to a variety of control systems, so that it will not be described in detail.

The slave apparatus 90 includes a force sensor (torque sensor) 91, a rotation angle sensor 93, and the motor 95 as components used to perform drive control over the arm and present haptic sensation. A driving signal corresponding to the amount of control calculated by the control apparatus 79 is transmitted to the motor 95 of the slave apparatus 90. The motors 95 are provided, for example, to the plurality of joint portions of the arm, and rotate and drive the respective joint portions. The motor 95 may be, for example, a servo motor. The motor 95 is driven in accordance with the amount of control calculated by the control apparatus 79, thereby operating the arm as instructed by a surgeon via the master apparatus 60. In addition, in the case where the surgical instrument includes a drivable section, the control apparatus 79 can transmit a driving signal for a motor for operating the drivable section. The motor is driven in accordance with the amount of control calculated by the control apparatus 79, thereby operating the surgical instrument as instructed by a surgeon via the master apparatus 60.

The force sensor 91 detects external force acting on a surgical instrument. The force sensors 91 are provided, for example, to the plurality of joint portions of the arm, and detect force (torque) acting on the respective joint portions. For example, the rotation angle sensors 93 are provided to a plurality of joint portions of the arm, and detect the rotation angles of the respective joint portions. The rotation angle sensor 93 may be, for example, an encoder. The information detected by these force sensors 91 and rotation angle sensors 93 is transmitted to the control apparatus 79. The control apparatus 79 consecutively grasps the current state of the arm on the basis of the information, and calculates the amount of control described above by taking even the current state of the arm into consideration.

Here, force acting on the surgical instrument attached to the front end of the arm can be reflected in force acting on each joint portion which is detected by the force sensor 91. The control apparatus 79 extracts a component of the force acting on the surgical instrument from the force acting on each joint portion which is detected by the force sensor 91, and calculates the amount of control over the motor 65 of the master apparatus 60. The motor 65 may be, for example, a servo motor. The control apparatus 79 drives the arm in accordance with the force acting on the surgical instrument to impart, for example, resistance to an operation input by a surgeon to the operation portion, thereby presenting the force acting on the surgical instrument to the surgeon. The medical robot system 1 has functions of detecting force acting on a surgical instrument, and feeding the force back to a surgeon in this way.

Next, the system for transmitting vibration detected on the slave apparatus 90 side to a surgeon will be described. The slave apparatus 90 includes the tactile vibration sensor 97 and the aural vibration sensor 99 as elements used to transmit vibration to a surgeon. The tactile vibration sensor 97 and the aural vibration sensor 99 may be attached, for example, to the proximal end side of a surgical instrument. The tactile vibration sensor 97 detects tactile vibration generated in the surgical instrument, and the aural vibration sensor 99 detects aural vibration (i.e., sound) generated in the surgical instrument. The tactile vibration sensor 97 may be, for example, an acceleration sensor. The aural vibration sensor 99 may be, for example, a condenser microphone.

A signal indicating tactile vibration detected by the tactile vibration sensor 97 is input to the first vibration transmission portion 70. The first vibration transmission portion 70 generates a driving signal for a vibration generating source 67 of the master apparatus 60 on the basis of the input signal indicating tactile vibration. Specifically, the first vibration transmission portion 70 uses an amplifier 71 to perform an amplification process on the input signal indicating tactile vibration, and then uses a frequency characteristic correction circuit 73 to perform a correction process on a vibration frequency. Further, a bandpass filter 75 is used to perform a filtering process, and the input signal indicating tactile vibration is then output to a driving circuit 77. The driving circuit 77 drives the vibration generating source 67 of the master apparatus 60 on the basis of the input signal. This causes the vibration corresponding to the tactile vibration detected by the slave apparatus 90 to be generated by the vibration generating source 67, and causes the tactile vibration generated in the surgical instrument to be transmitted to a surgeon. The vibration generating source 67 may be, for example, any one of a piezo-vibration actuator, a voice coil motor type vibration actuator, a linear vibration actuator, an eccentric rotating mass (ERM) type vibration actuator, or an electroactive polymer artificial muscle (EPAM) type vibration actuator.

A signal indicating aural vibration detected by the aural vibration sensor 99 is input to the second vibration transmission portion 80. The second vibration transmission portion 80 outputs a driving signal for a speaker 69 of the master apparatus 60 on the basis of the input signal indicating aural vibration. Specifically, the second vibration transmission portion 80 uses an amplifier 81 to perform an amplification process on the input signal indicating aural vibration, and then uses a frequency characteristic correction circuit 83 to perform a correction process on a vibration frequency. Further, a bandpass filter 85 is used to perform a filtering process, and the input signal indicating tactile vibration is then output to a driving circuit 87. The driving circuit 87 drives the speaker 69 of the master apparatus 60 on the basis of the input signal. This causes the sound corresponding to the aural vibration detected by the slave apparatus 90 to be output from the speaker 69, and causes the aural vibration generated in the surgical instrument to be transmitted to a surgeon.

Note that some or all of the functions of the control apparatus 79 may be included in at least one of the slave apparatus 90 or the master apparatus 60. In addition, some or all of the respective components of the first vibration transmission portion 70 and the second vibration transmission portion 80 may be included in at least one of the slave apparatus 90 or the master apparatus 60.

2. Overall Configuration Example Haptic Presentation Apparatus (Master Apparatus)

Figure 2:
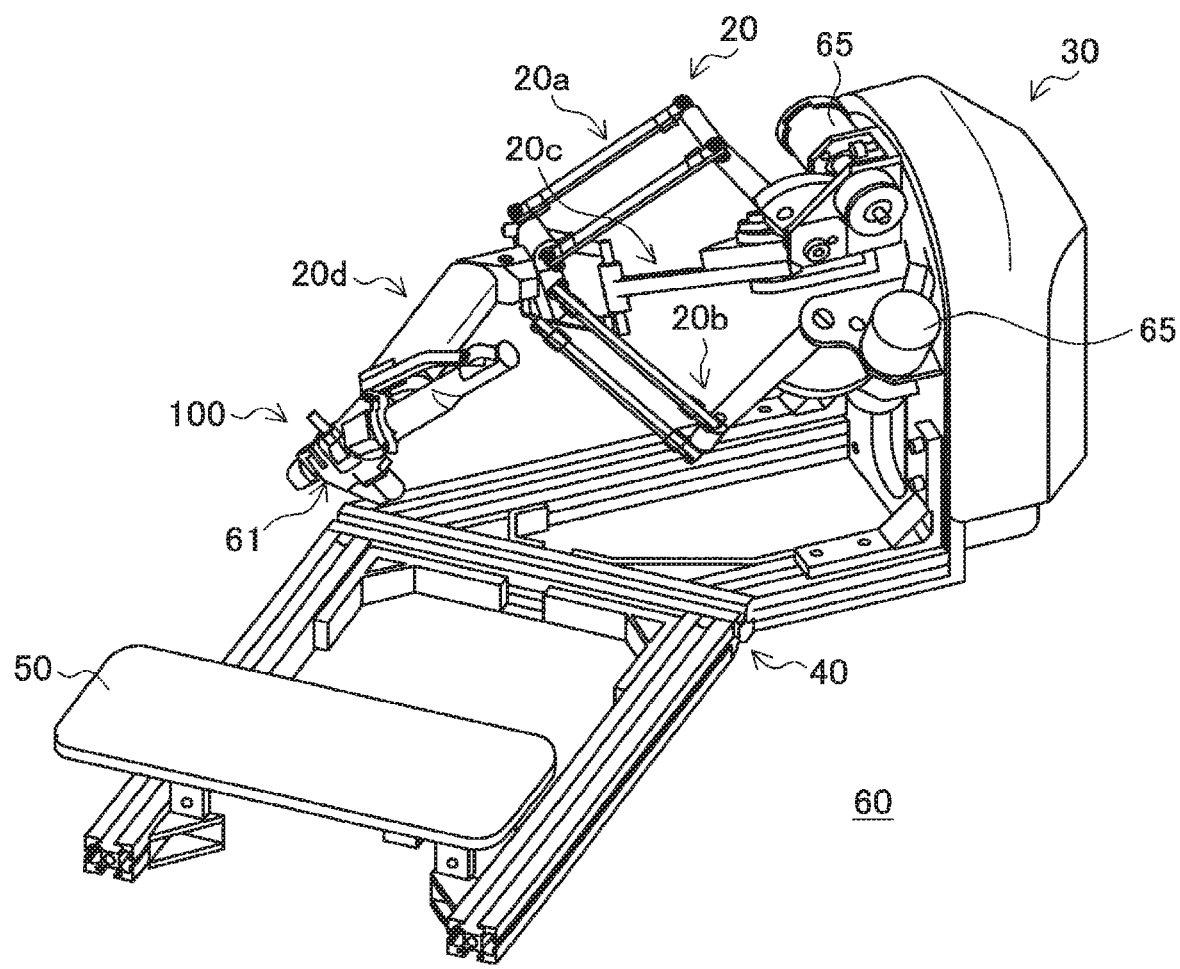
FIG. 2 is a perspective view illustrating the haptic presentation apparatus according to the embodiment.

Next, with reference to FIG. 2, the overall configuration of the master apparatus 60 serving as the haptic presentation apparatus according to the present embodiment will be described. FIG. 2 illustrates a perspective view of the master apparatus 60 according to the present embodiment. The master apparatus 60 illustrated in FIG. 2 includes a supporting arm portion 20, a main body portion 30, a base portion 40, and an operation portion 100. The base portion 40 is the base part of the master apparatus 60, and may be configured, for example, by combining aluminum frame members. However, the configuration of the base portion 40 is not limited to the example. A supporting base 50 is attached to the base portion 40. A surgeon operates the operation portion 100 with his or her elbow or arm on the supporting base 50, thereby making it possible to obtain operational stability. Note that the supporting base 50 does not have to be attached to the base portion 40, or does not have to be included in the components of the master apparatus 60.

The supporting arm portion 20 is supported by the main body portion 30 on the proximal end side. The operation portion 100 is attached to the front end side of the supporting arm portion 20. The supporting arm portion 20 includes a first arm portion 20a, a second arm portion 20b, a third arm portion 20c, and a fourth arm portion 20d. The respective front end sides of the first arm portion 20a, the second arm portion 20b, and the third arm portion 20c are coupled to the fourth arm portion 20d, and the proximal end sides are coupled to the main body portion 30. The main body portion 30 includes the three motors 65 (one of them is not illustrated) that control the rotation of the coupled parts between the first arm portion 20a, the second arm portion 20b and the third arm portion 20c, and the main body portion 30.

The first arm portion 20a, the second arm portion 20b, and the third arm portion 20c each include a plurality of link portions coupled in series such that the plurality of link portions can pivot with respect to each other. In addition, the coupled parts between the first arm portion 20a, the second arm portion 20b and the third arm portion 20c, and the fourth arm portion 20d are also coupled so as to pivot with respect to each other. Further, the coupled parts between the first arm portion 20a, the second arm portion 20b and the third arm portion 20c, and the main body portion 30 are also coupled so as to pivot with respect to each other.

The coupled parts between the plurality of these link portions or between the arm portions can serve as joint portions, the angle of each link portion or arm portion can freely change around the joint portion. With this arrangement, the spatial position of the operation portion 100 attached to the front end side of the supporting arm portion 20 can freely change. In addition, the fourth arm portion 20d includes a plurality of coupled arms, and each arm is capable of axial rotation. With this arrangement, the direction of the operation portion 100 attached to the front end side of the supporting arm portion 20 can freely change.

The coupled parts between the first arm portion 20a, the second arm portion 20b and the third arm portion 20c, and the main body portion 30 are each provided with an encoder for detecting the rotation angle of each arm portion. In addition, the fourth arm portion 20d is provided with a plurality of encoders for detecting the axial rotation angles of the respective arms. An encoder is an example of sensors that detect rotation angles, and may be replaced with another sensor. Signals indicating rotation angles which are detected by these encoders are transmitted to the control apparatus 79 described above.

The operation portion 100 functions as a grasping interface for operating a surgical instrument supported by a slave apparatus that is not illustrated. A surgeon changes the position or direction of the operation portion 100, thereby changing the attitude of the supporting arm portion 20 to change the rotation angle of a joint portion or axial rotation angle of an arm. The connected part between the operation portion 100 and the fourth arm portion 20d is provided with the force sensor 61. The force sensor 61 detects force input by a surgeon to the operation portion 100.

The control apparatus 79 described above controls the attitude of the arm of a slave apparatus on the basis of the information of a rotation angle detected by an encoder included in the master apparatus 60, and changes the position or direction of a surgical instrument supported by the slave apparatus. At this time, the control apparatus 79 detects external force acting on the surgical instrument of the slave apparatus, and performs drive control over the three motors 65 on the basis of the external force, thereby imparting reaction force to the movement of the operation portion 100 operated by a surgeon to present haptic sensation for the movement operation of the operation portion 100 to the surgeon.

In addition, a user performs a grasping operation of the operation portion 100 to cause the control apparatus 79 to acquire a signal indicating the operation amount of the grasping operation from the operation portion 100, and causes a surgical instrument attached to a slave apparatus to perform a grasping operation on the basis of the signal. At this time, the control apparatus 79 may detect reaction force against the grasping operation of the surgical instrument attached to the slave apparatus, and perform drive control on the basis of the reaction force over a motor that is included in the operation portion 100, but not illustrated, thereby presenting haptic sensation for the grasping operation of the operation portion 100 to a surgeon.

In addition, the operation portion 100 includes a vibration generating source such as a voice coil motor that is not illustrated. The first vibration transmission portion 70 described above detects tactile vibration generated in a surgical instrument of a slave apparatus, and performs drive control over the vibration generating source on the basis of the tactile vibration, thereby presenting tactile sensation to a surgeon. Further, the master apparatus 60 includes a speaker that is not illustrated. The second vibration transmission portion 80 described above detects aural vibration generated in a surgical instrument of a slave apparatus, and drives the speaker on the basis of the aural vibration, thereby outputting sound.

Note that the supporting arm portion 20 including the rotation angle sensors for detecting the rotation angles of the joint portions and the axial rotation angles of the arms may be constituted from a conventionally known supporting arm apparatus and thus detailed description of a configuration of the supporting arm portion 20 is omitted.

Figure 3:
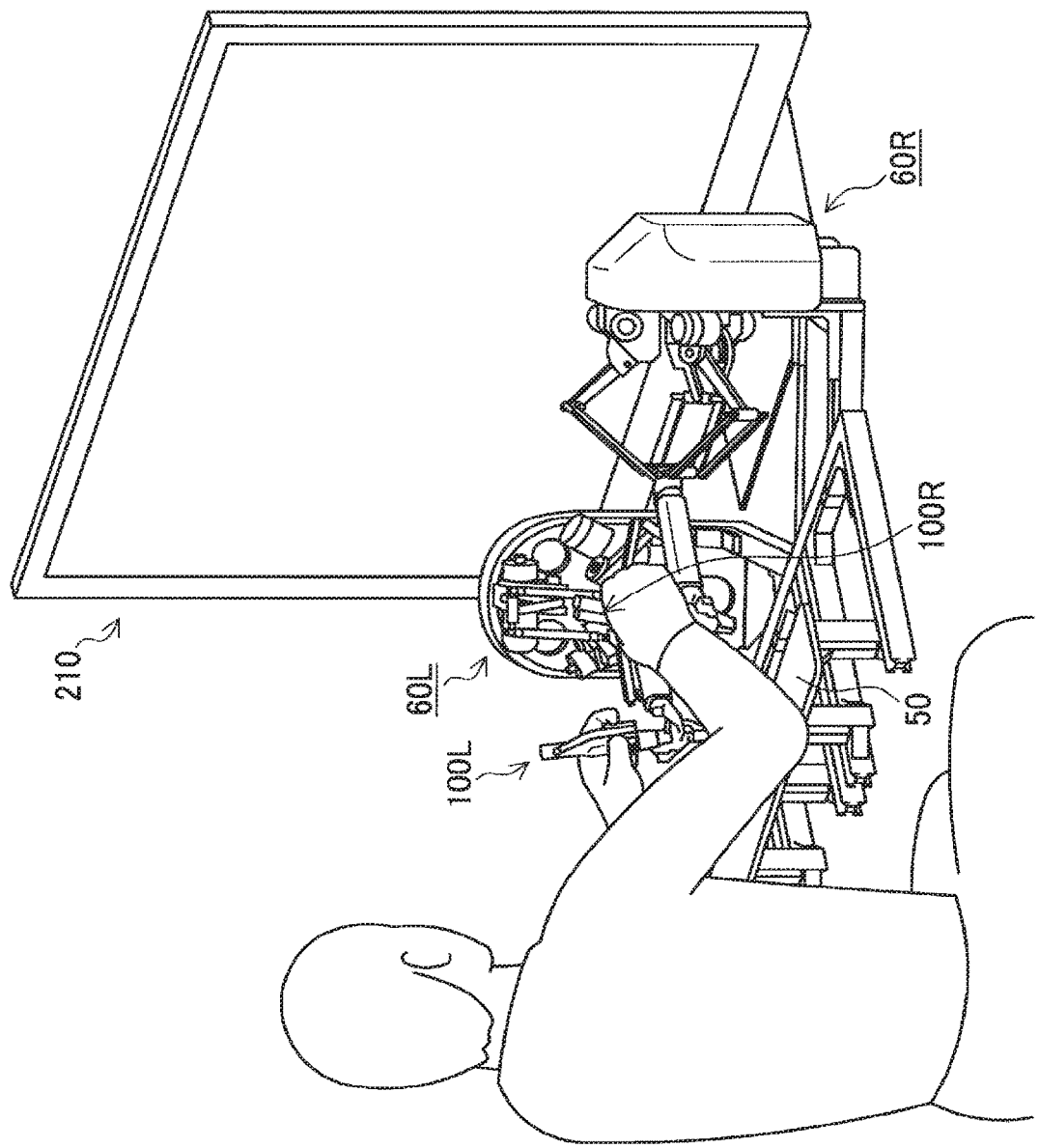
FIG. 3 is an explanatory diagram illustrating a use example of the haptic presentation apparatus according to the embodiment.

FIG. 3 illustrates a use example of the master apparatus 60 according to the present embodiment. In FIG. 3, two master apparatuses 60R and 60L for a right hand and a left hand are both provided. A surgeon puts both arms or both elbows on the supporting base 50, and uses the right hand and the left hand to grasp the operation portions 100R and 100L, respectively. In this state, the surgeon operates the operation portions 100R and 100L while watching a monitor 210 showing a surgical site. The surgeon may displace the positions or directions of the respective operation portions 100R and 100L to remotely operate the positions or directions of surgical instruments attached to slave apparatuses each of which is not illustrated, or use each surgical instrument to perform a grasping operation.

3. Operation Portion

Next, a configuration example of the operation portion 100 attached to the master apparatus 60 according to the present embodiment will be described.

3-1. Overall Configuration Example

Figure 4:
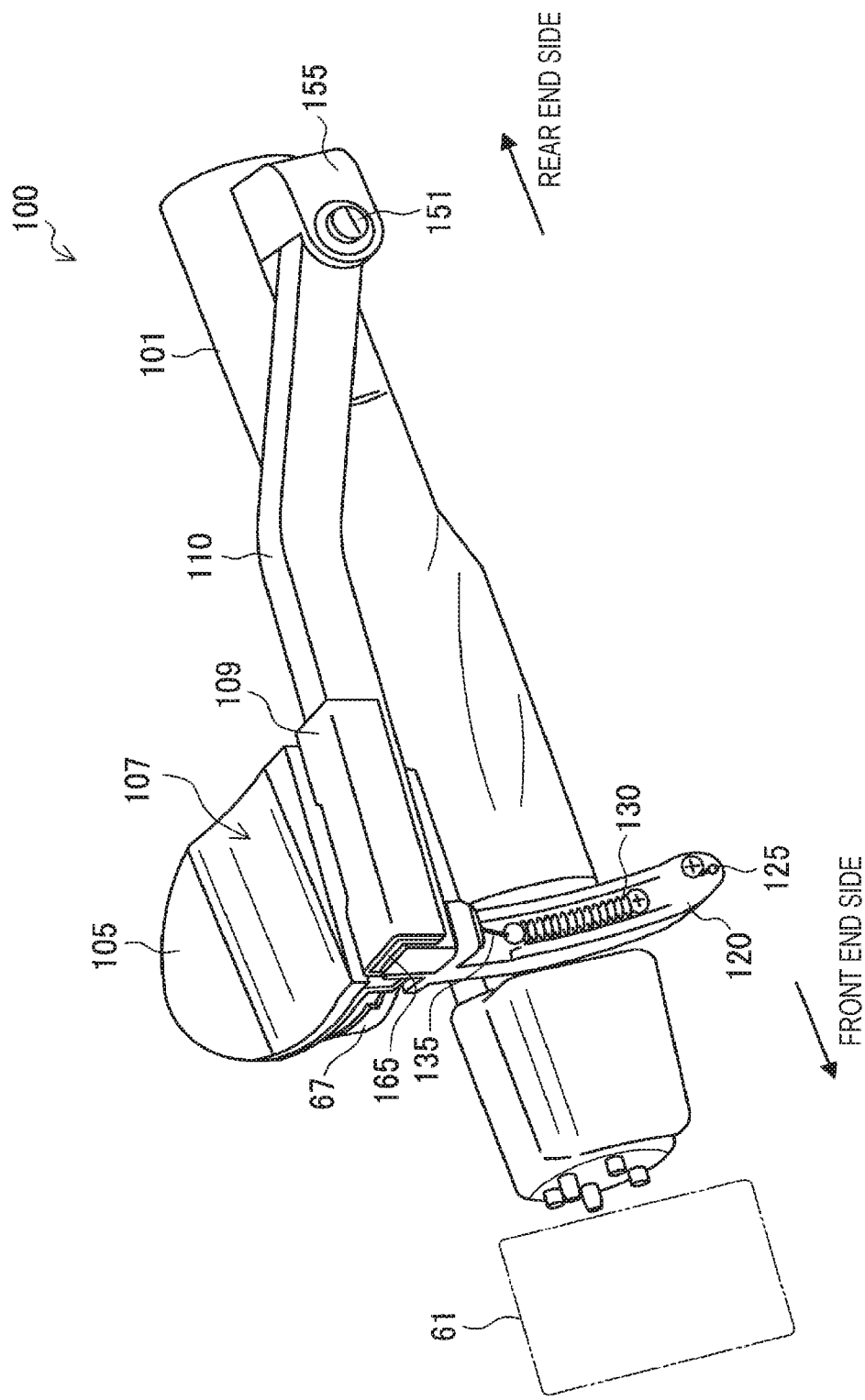
FIG. 4 is a perspective view illustrating the haptic presentation apparatus according to the embodiment.
Figure 5:
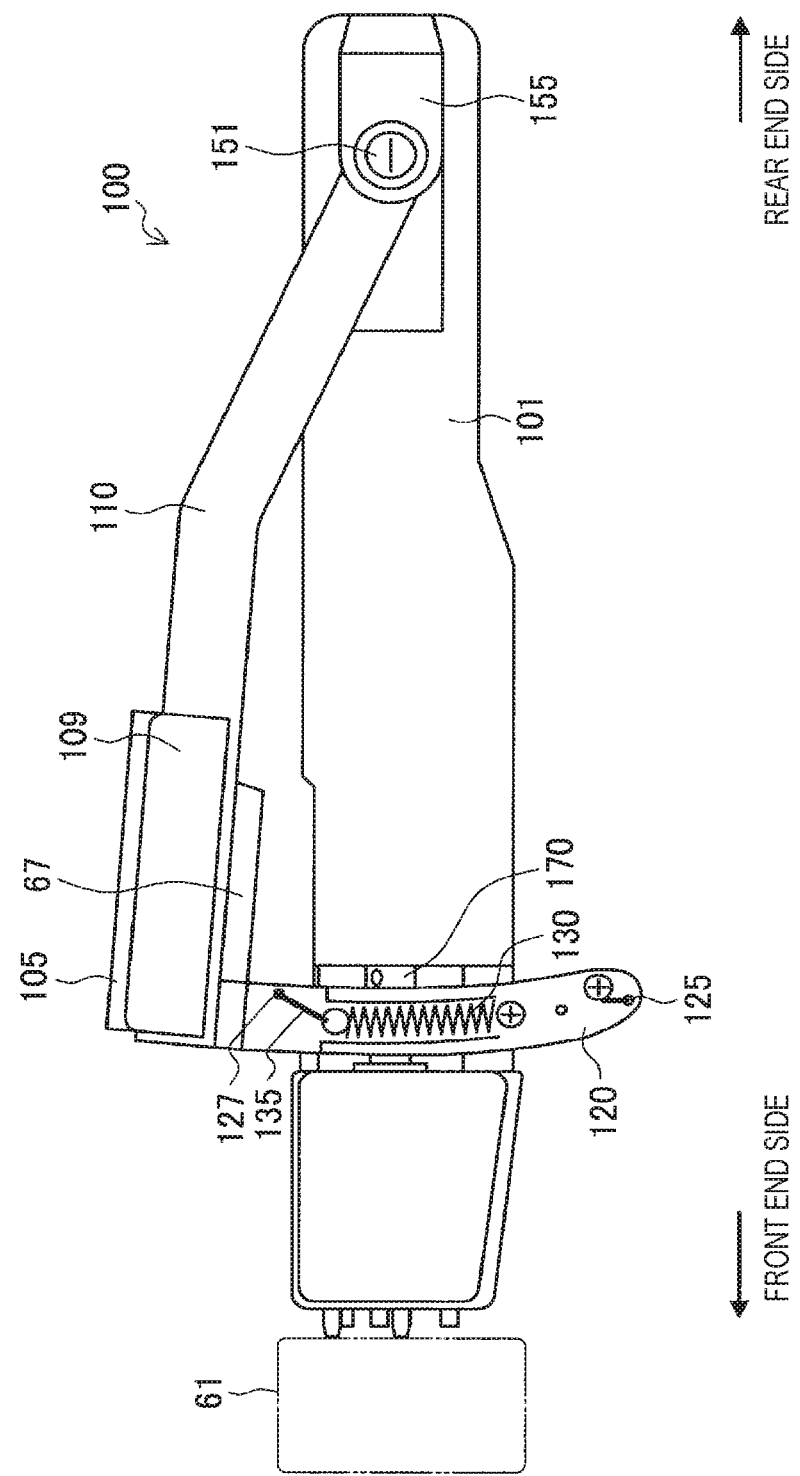
FIG. 5 is a side view of the haptic presentation apparatus according to the embodiment.
Figure 6:
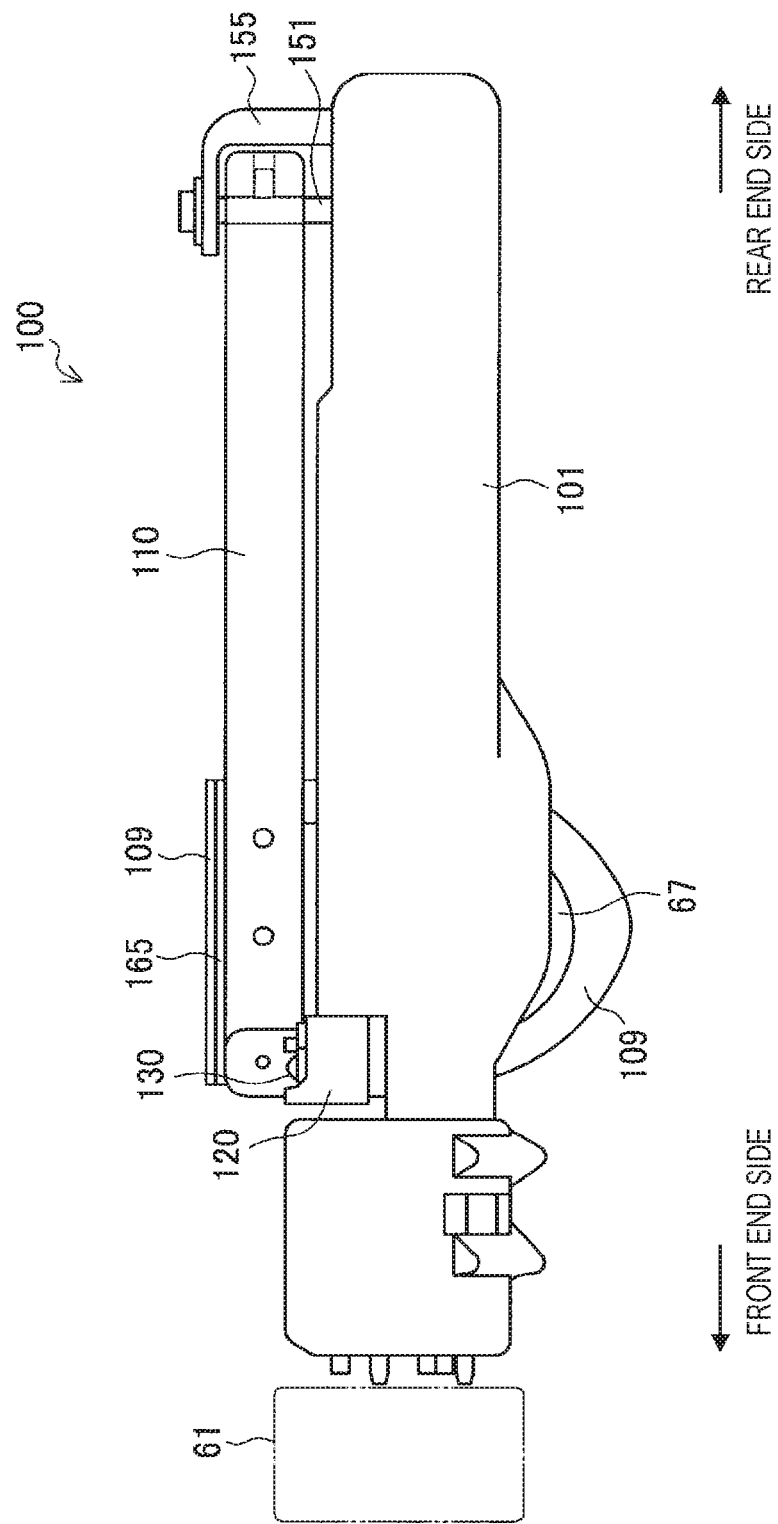
FIG. 6 is a bottom view of the haptic presentation apparatus according to the embodiment.
Figure 7:
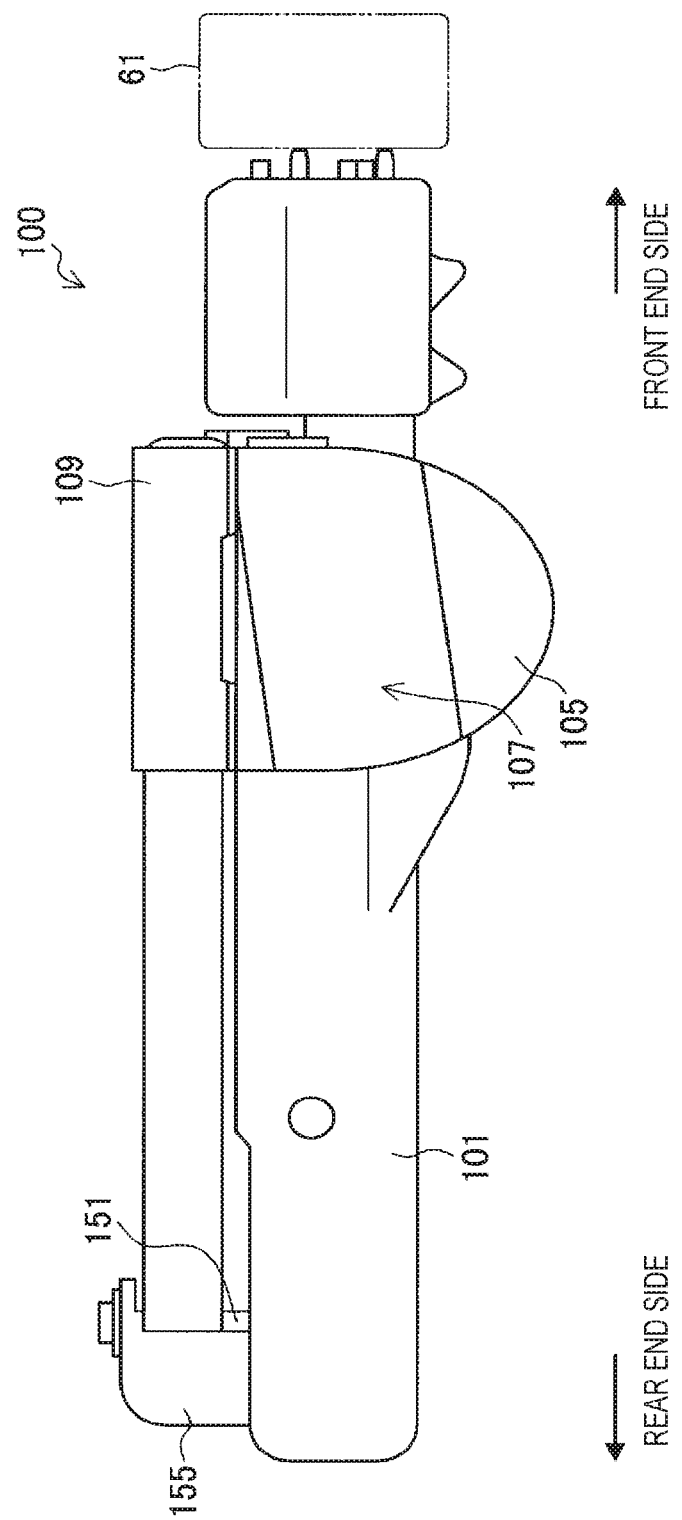
FIG. 7 is a top view of the haptic presentation apparatus according to the embodiment.
Figure 8:
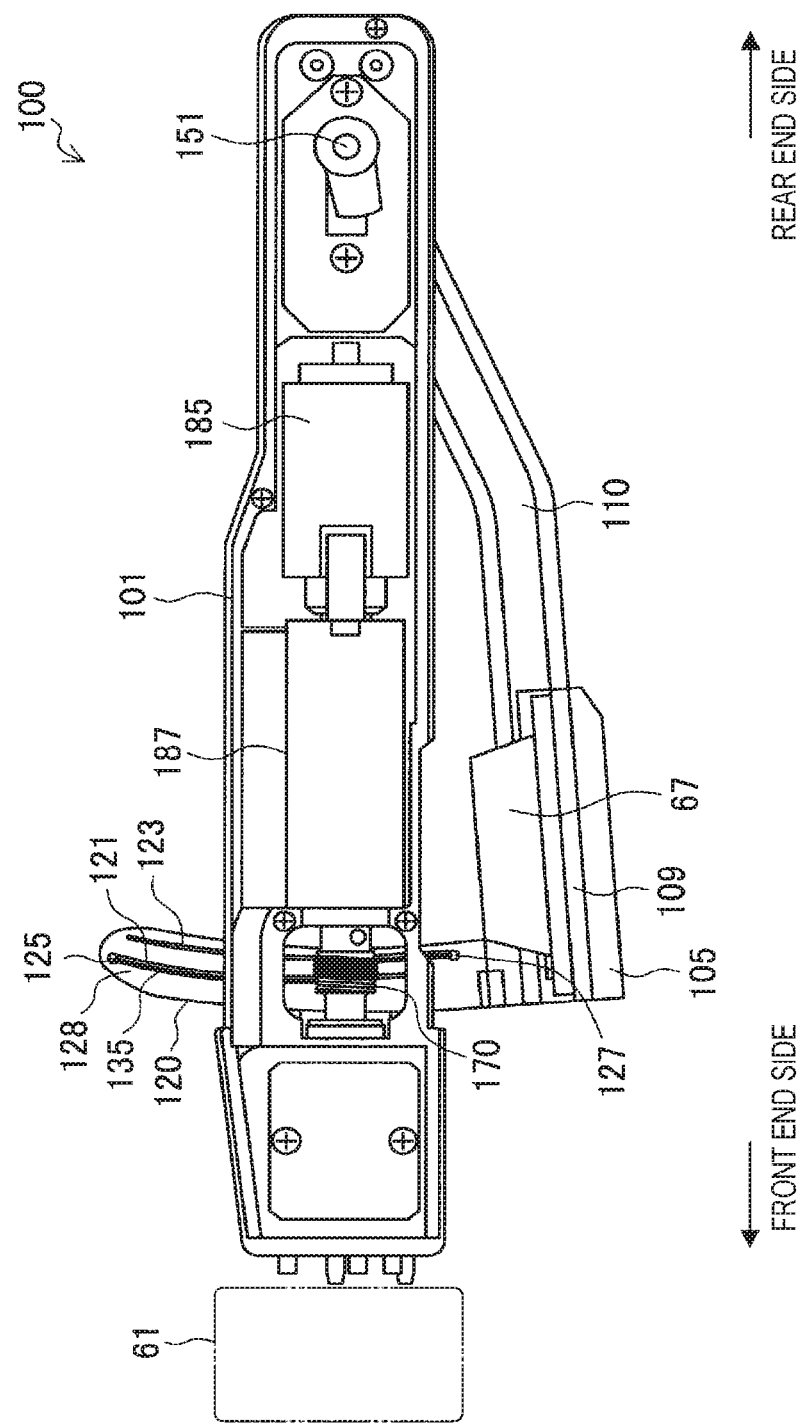
FIG. 8 is an explanatory diagram illustrating an internal structure of the haptic presentation apparatus according to the embodiment.

First, with respect to FIGS. 4 to 8, an overall configuration example of the operation portion 100 will be described. FIG. 4 is a perspective view of the operation portion 100, and FIG. 5 is a side view showing the operation portion 100 of FIG. 4 from the front side. In addition, FIG. 6 is a bottom view showing the operation portion 100 of FIG. 4 from the bottom side, and FIG. 7 is a top view showing the operation portion 100 of FIG. 4 from the top side. Further, FIG. 8 is an explanatory diagram illustrating the internal structure of the operation portion 100, and is an internal perspective view showing the operation portion 100 of FIG. 4 from the back side.

The inside of the operation portion 100 includes a housing 101 that houses a motor 187 and an encoder 185. The outer shape of the housing 101 is like a long stick as a whole to facilitate a user to grasp. That is, the operation portion 100 is a so-called stylus-type grasping interface. The operation portion 100 is attached to the fourth arm portion 20d of the master apparatus 60 on the front end side. The connected part between the front end side of the operation portion 100 and the fourth arm portion 20d is provided with the force sensor 61.

The encoder 185 is an example of rotation angle sensors that detect the rotation angles of the motors 187. Sensors that detect the rotation angles of the motors 187 are not limited to the encoder 185. The output shaft of the motor 187 is disposed along the longitudinal direction of the operation portion 100, and is connected to a pulley 170 disposed on the front end side of the operation portion 100. With this arrangement, the pulley 170 is capable of axial rotation with the driving torque of the motor 187. The pulley 170 is exposed to the outside of the housing 101, and an outer peripheral surface 171 of the pulley 170 faces a rail portion 120 on a side of the operation portion 100. The outer peripheral surface 171 of the pulley 170 includes a part of a virtual conical surface having the cone axis that agrees with the axis of the output shaft of the motor 187.

The rear end side of the housing 101 is provided with a rotating shaft member 151. Both ends of the rotating shaft member 151 are supported by a bearing portion 155 and the housing 101. The master frame 110 serving as a frame portion is coupled to the rotating shaft member 151 so as to freely pivot on the rotating shaft member 151. The master frame 110 that pivots on the rotating shaft member 151, and a component attached to the master frame 110 correspond to a movable portion in the present disclosure as a whole.

The master frame 110 is a long member disposed on a side of operation portion 100 along the longitudinal direction, and extends along the direction crossing the axial direction of the rotating shaft member 151. At an appropriate position on the front end side of the master frame 110, a contact portion 105 is provided that has a surface crossing the rotation direction of the master frame 110 and extending along the longitudinal direction of the operation portion 100. The contact portion 105 is attached to the master frame 110 with a support portion 109. The contact portion 105 includes, for example, a placement portion 107 on which an index finger of a user is placed. The placement portion 107 is shaped to be recessed like an arch to be easily adapted to the shape of a finger of a surgeon. A surgeon can grasp the operation portion 100 like he or she grips a writing pen, and then pivot the master frame 110 with an index finger put on the placement portion 107.

In addition, the vibration generating source 67 is provided in the vicinity of the contact portion 105. Specifically, the vibration generating source 67 is attached to the rear surface side of the surface of the support portion 109 on which the contact portion 105 is disposed. In the present embodiment, a voice coil motor type vibration actuator is used as the vibration generating source 67, but another vibration generating source may also be used. The vibration generating source 67 generates vibration to be transmitted to a finger of a surgeon put on the placement portion 107, and presents tactile vibration that acts on a surgical instrument of a slave apparatus to the surgeon.

In addition, the rail portion 120 that extends toward the rotation direction of the master frame 110 is provided on the front end side of the master frame 110. The rail portion 120 has a substantially arcuate outer shape, and pivots along the extending direction of the rail portion 120 with the pivoting master frame 110. That is, the rail portion 120 rotates around the rotating shaft member 151. The rail portion 120 has an opposed surface 128 that is opposed to the outer peripheral surface 171 of the pulley 170. The opposed surface 128 includes a part of a virtual conical surface having the rotating shaft member 151 as a cone axis.

A wire 135 is wound around a wire groove 173 of the pulley 170. Both end portions of such the wire 135 are arranged on the rail portion 120 and the central portion of the wire 135 is wound around the pulley 170. The wire 135 functions as a member that transmits power and driving torque generated by the motor 187 is transmitted to the rail portion 120 via the pulley 170 and the wire 135. Meanwhile, the rotation torque of the rail portion 120 can also be transmitted to the motor 187 via the wire 135 and the pulley 170 with the pivoting rail portion 120.

As described above, the force sensor 61 is provided to the connected part between the operation portion 100 and the fourth arm portion 20d of the supporting arm portion 20. The force sensor 61 may be a six-axis force sensor that detect the force and torsion of six-axis components in three directions which are input to the operation portion 100 that is operated by a surgeon. When translational force or force in the torsional direction is imparted to the operation portion 100, the force sensor 61 generates the output corresponding to the moment of the force. In the case where the position and direction of a surgical instrument of a slave apparatus are subjected to force control, the control apparatus 79 described above uses the force sensor 61 to detect the force moment input to the operation portion 100, and controls the attitude of the arm of the slave apparatus on the basis of the force moment. This makes it possible to smoothly control the position and direction of the surgical instrument attached to the slave apparatus.

In the operation portion 100, the motor 187 and the encoder 185 are each connected electrically to the control apparatus 79 described above via a cable that is not illustrated or the like. The force sensor 61 that detects force input to the operation portion 100 is also connected to the control apparatus 79 electrically. In addition, the vibration generating source 67 is electrically connected to the first vibration transmission portion 70 described above. This causes detection signals of the encoder 185 and the force sensor 61 to be output to the control apparatus 79, and causes a driving signal to be input to the motor 187 from the control apparatus 79. In addition, a driving signal is input to the vibration generating source 67 from the driving circuit of the first vibration transmission portion 70.

Figure 9:
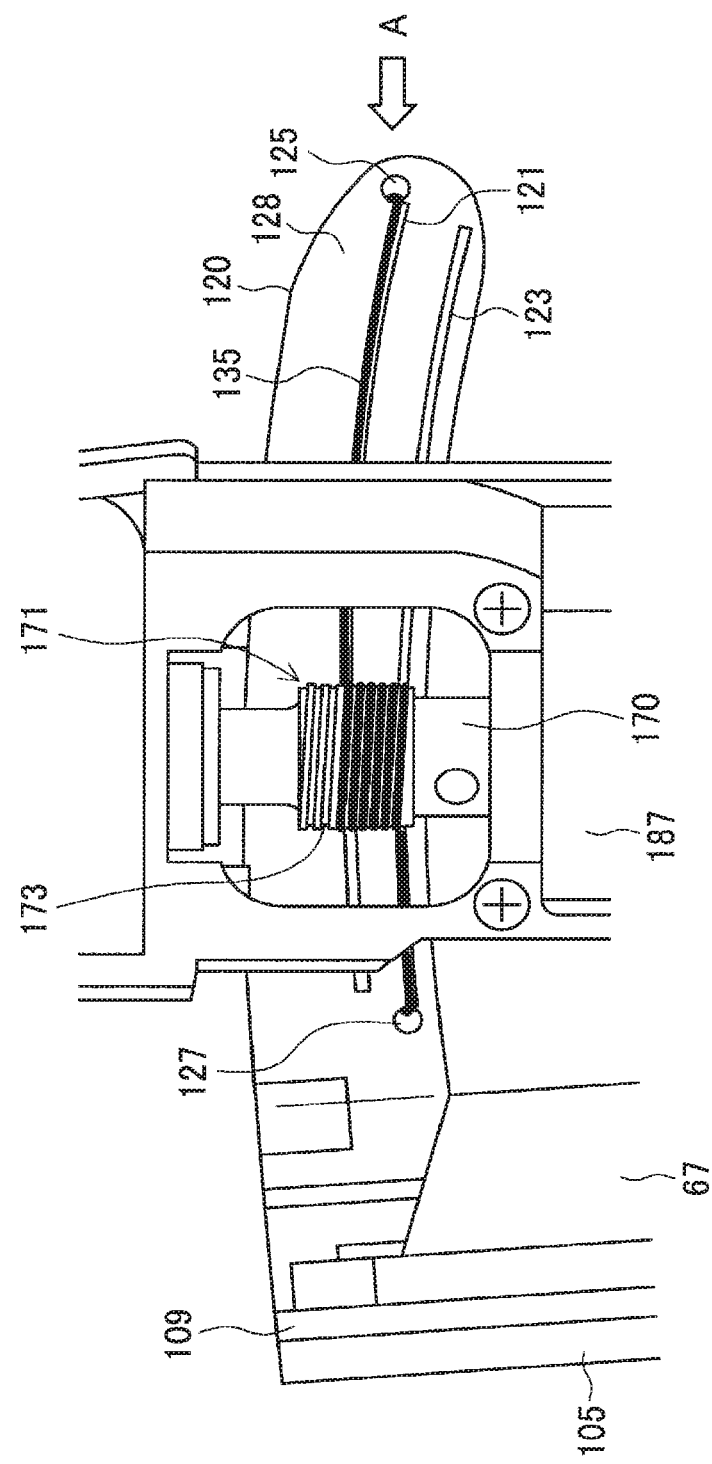
FIG. 9 is an explanatory diagram illustrating a magnified power transmission mechanism.
Figure 10:
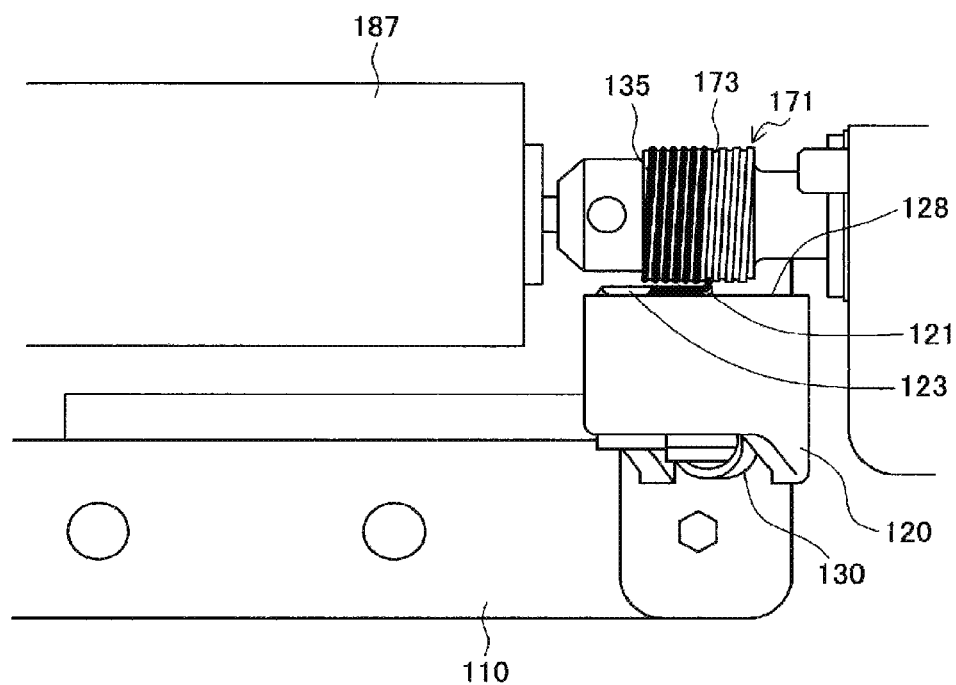
FIG. 10 is a diagram showing the power transmission mechanism illustrated in FIG. 9 from a direction of an arrow A.
Figure 11:
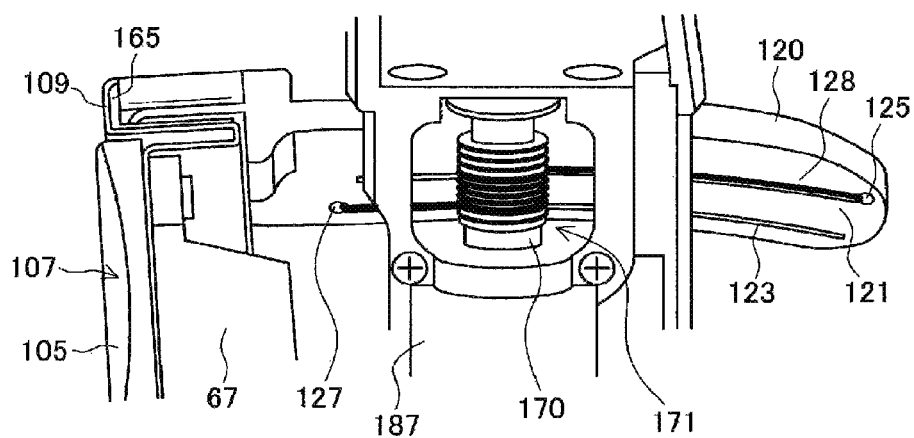
FIG. 11 is a perspective view of the power transmission mechanism.

FIG. 9 is an explanatory diagram illustrating the magnified area around the pulley 170 and the rail portion 120. FIG. 10 is a view as seen from an arrow A of FIG. 9. FIG. 11 is a perspective view illustrating the magnified area around the pulley 170 and the rail portion 120. The driving torque of the motor 187 provided to the operation portion 100 can be transmitted to the rail portion 120 via the pulley 170 and the wire 135. In addition, rotation torque obtained by a surgeon pivoting the rail portion 120 can be transmitted to the motor 187 via the wire 135 and the pulley 170.

The pulley 170 rotated by the driving force of the motor 187 has the outer peripheral surface 171 including a part of the virtual conical surface having the cone axis agreeing with the axis of the output shaft of the motor 187. That is, the outer peripheral surface 171 has a taper shape. The outer peripheral surface 171 of the pulley 170 is provided with the spiral wire groove 173 spirally circulating around the outer peripheral surface 171. The rail portion 120 has the opposed surface 128 that is opposed to the outer peripheral surface of the pulley 170. The opposed surface 128 includes a part of a virtual conical surface having the axis of the rotating shaft member 151 as a cone axis. A first guide portion 121 and a second guide portion 123 for guiding the wire 135 are provided on the opposed surface 128 of the rail portion 120 along the circumferential direction of the second virtual conical surface. The first guide portion 121 and the second guide portion 123 are each formed, for example, as a wall portion with a predetermined length which protrudes from the opposed surface 128.

The wire 135 serving as means for transmitting the rotation torque of the pulley 170 to the rail portion 120 is wound around the pulley 170. The wire 135 is wound along the spiral wire groove 173 formed on the outer peripheral surface 171 of the pulley 170. The wire 135 led out from the front side of the pulley 170 which has a larger diameter is guided by the first guide portion 121 to be arranged. In addition, the wire 135 led out from the rear side of the pulley 170 which has a smaller diameter is guided by the second guide portion 123 to be arranged.

The end portion of the wire 135 arranged along the first guide portion 121 is led to the rear side of the opposed surface 128 via a hole 125 formed in the rail portion 120 and fixed by a fixing means such as a screw. In addition, between the both end portions of the wire 135, the end portion of the wire 135 arranged along the second guide portion 123 is led to the rear side of the opposed surface 128 via a hole 127 formed in the rail portion 120 and fixed to one end of a spring 130 fixed to the rear side of the rail portion 120. This imparts tension to the wire 135 with the elastic force of the spring 130, which makes it possible to prevent the wire 135 from being loose on the pulley 170 and the rail portion 120. The spring 130 is an example of components for imparting tension to the wire 135, and other tension generating portion may be adopted.

Here, since the opposed surface of the rail portion 120 includes a part of the conical surface, the tension of the wire 135 can cause the wire 135 to slide over the opposed surface 128 of the rail portion 120 and be displaced from the sending-out position to the pulley 170 or the winding position from the pulley 170. Thus, the opposed surface 128 of the rail portion 120 is provided with the first guide portion 121 and the second guide portion 123, and the wire 135 on the rail portion 120 is pressed against the first guide portion 121 or the second guide portion 123 by the tension. This prevents the displacement of the wire 135. At this time, the wire 135 arranged along the first guide portion 121 and the second guide portion 123 is positioned at the winding position of the pulley 170 or the sending-out position from the pulley 170 irrespective of the rotation angle of the pulley 170 and the position of the rail portion 120. Thus, the wire 135 wound around the pulley 170 is appropriately arranged along the wire groove 173, thereby allowing power to be smoothly transmitted between the rail portion 120 and the pulley 170.

Figure 12:
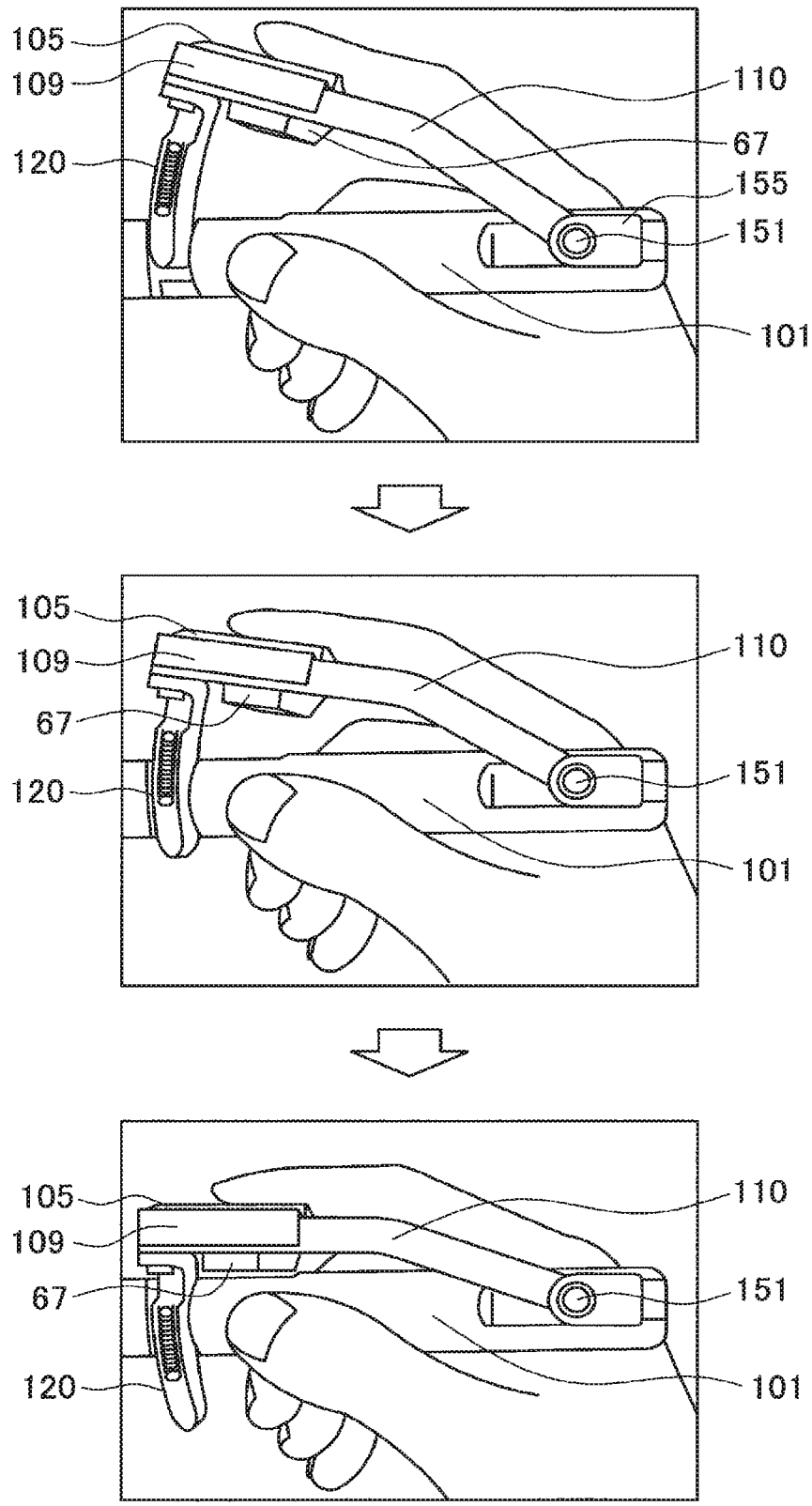
FIG. 12 is an explanatory diagram illustrating a use state of the haptic presentation apparatus.

FIG. 12 illustrates that a surgeon pivots the master frame 110 and the rail portion 120. The upper part of FIG. 12 illustrates that the master frame 110 and the rail portion 120 are placed at the origin positions. At this time, the pulley 170 faces the front end portion of the rail portion 120. In addition, the middle part of FIG. 12 illustrates that the master frame 110 and the rail portion 120 are pushed into approximately the half of the movable area. At this time, the pulley 170 faces the central portion of the rail portion 120 (see FIG. 9). Further, the lower part of FIG. 12 illustrates that the master frame 110 and the rail portion 120 are pushed the most. At this time, the pulley 170 faces the opposed surface 128 on the base portion side of the rail portion 120. In this way, a surgeon uses an index finger or the like to push the contact portion 105, thereby making it possible to perform a grasping operation of the operation portion 100.

As the master frame 110 and the rail portion 120 pivot, the pulley 170 rotates and the output shaft of the motor 187 also rotates. The control apparatus 79 described above receives the information of the rotation angle of the motor 187 which is detected by the encoder 185, drives the drivable section of a surgical instrument of a slave apparatus on the basis of a change in the rotation angle, and causes the surgical instrument to perform a grasping operation. In addition, the first vibration transmission portion 70 described above drives the vibration generating source 67 on the basis of tactile vibration acting on the surgical instrument of the slave apparatus, and presents tactile sensation to the surgeon.

3-2. Vibration Transmission Suppressing Structure

Here, the operation portion 100 includes a vibration transmission suppressing structure for suppressing the transmission of vibration generated by the vibration generating source 67 used to present tactile sensation to a surgeon to the force sensor 61. That is, the force sensor 61 is a sensor that detects force generated by a surgeon operating the operation portion 100, so that the operation portion 100 is provided with a structure for suppressing the transmission of the vibration of the vibration generating source 67 to the force sensor 61.

Figure 13:
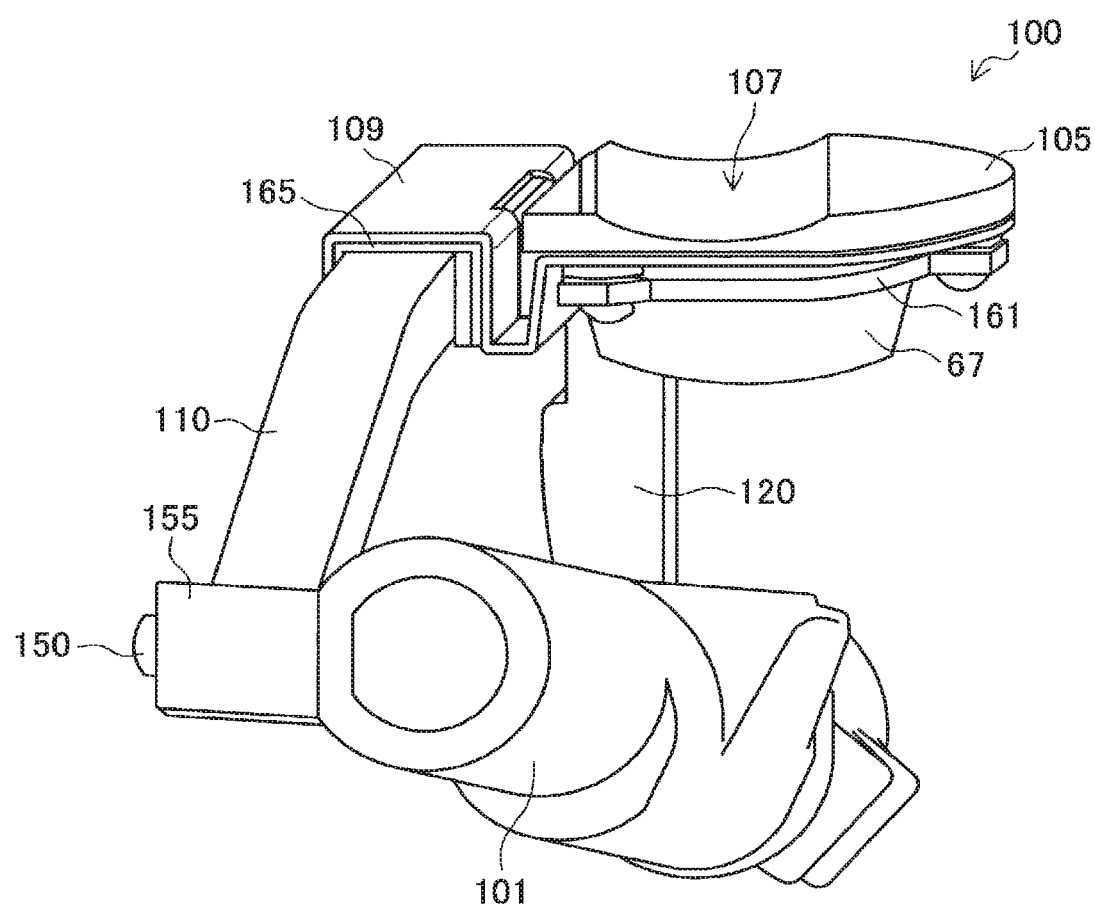
FIG. 13 is a perspective view illustrating a configuration example of a vibration transmission suppressing structure.
Figure 14:
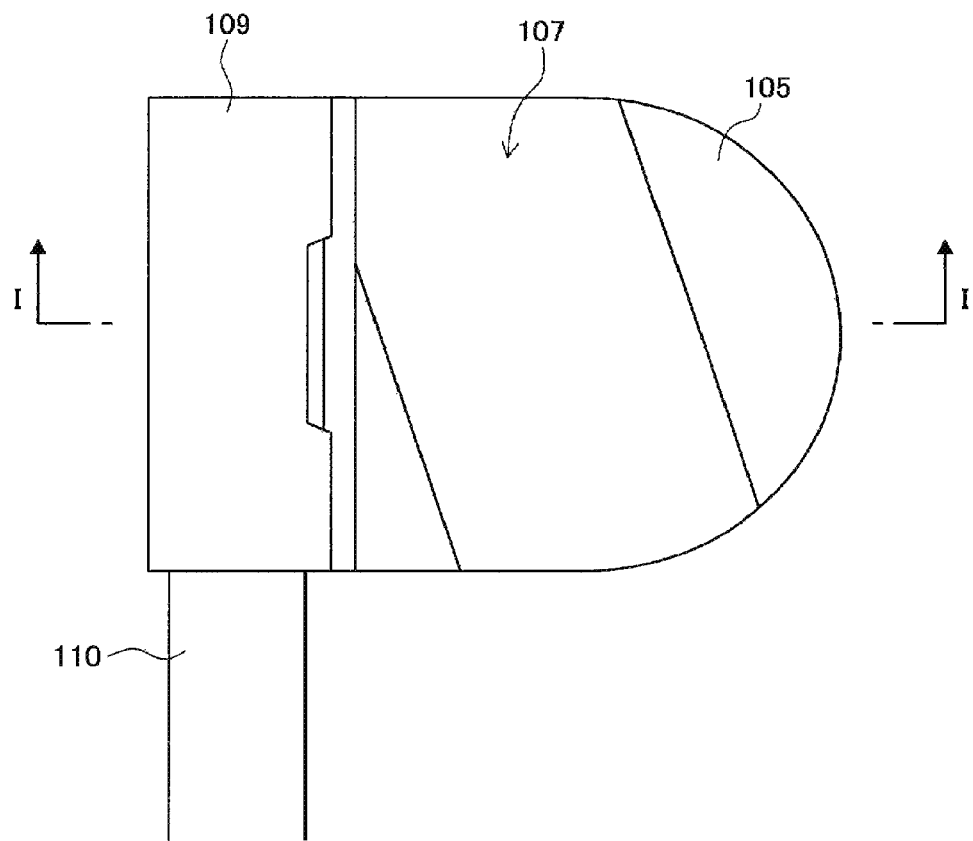
FIG. 14 is a top view illustrating a configuration example of the vibration transmission suppressing structure.
Figure 15:
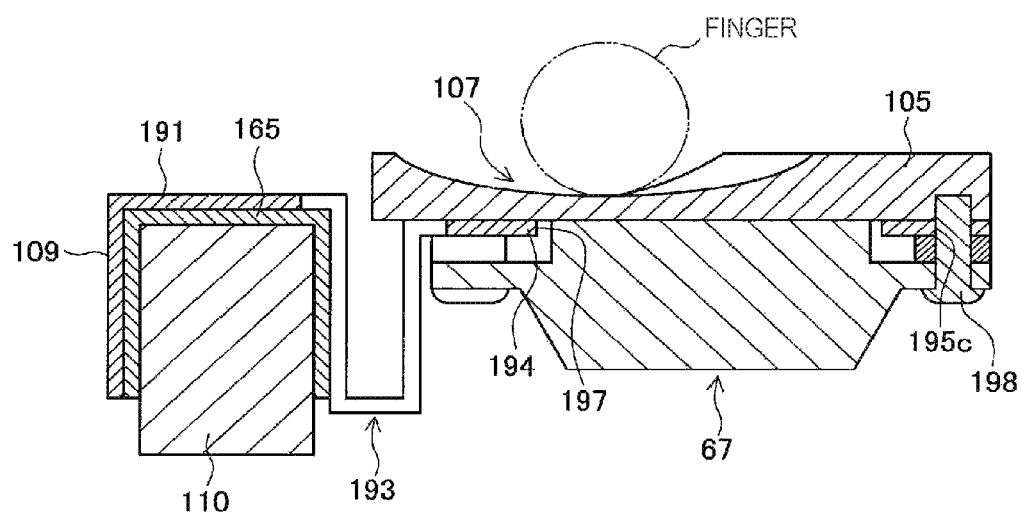
FIG. 15 is a cross-sectional view illustrating a configuration example of the vibration transmission suppressing structure.
Figure 16:
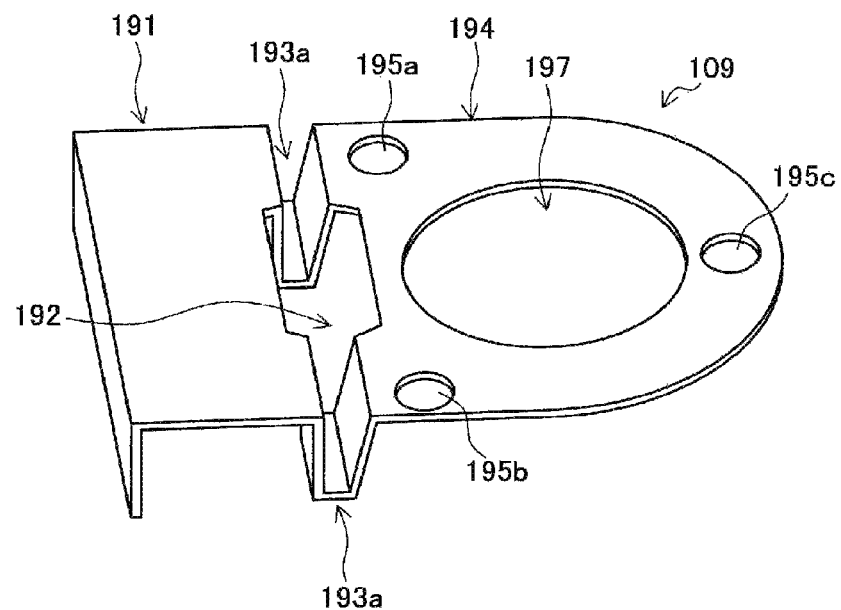
FIG. 16 is a perspective view illustrating a configuration example of a support portion that supports a contact portion.

FIGS. 13 to 16 are explanatory diagrams illustrating vibration transmission suppressing structures. FIG. 13 is a perspective view showing the operation portion 100 from the rear end side, FIG. 14 is a plan view illustrating the contact portion 105 supported by the master frame 110, and FIG. 15 is a cross-sectional view illustrating a configuration example of the vibration transmission suppressing structure. In addition, FIG. 16 is a perspective view of the support portion 109.

As described above, the contact portion 105 that comes into contact with a part of a surgeon such as an index finger is attached to the master frame 110 with the support portion 109. The support portion 109 is a member cantilevered by the master frame 110, and includes a frame connection portion 191, an elastic portion 193 and a fixation portion 194. The support portion 109 can include, for example, stainless steel. As illustrated in FIG. 16, the support portion 109 includes the frame connection portion 191 that forms a U-shaped cross section with a part of the elastic portion 193, the fixation portion 194 that has a plane shape substantially corresponding to the plane shape of the contact portion 105, and the elastic portion 193 that is provided between the frame connection portion 191 and the fixation portion 194.

The fixation portion 194 has three small holes 195*a*, 195*b* and 195*c*, and one large hole 197. Respective fixing screws 198 for attaching the contact portion 105 and the vibration generating source 67 are inserted into the three small holes 195*a*, 195*b* and 195*c*. In addition, a part of the vibration generating source 67 is inserted into the large hole 197 to enable the vibration generating source 67 to come into direct contact with the contact portion 105. This facilitates vibration generated by the vibration generating source 67 to be transmitted to a surgeon.

Meanwhile, the frame connection portion 191 of the support portion 109 is mounted on the master frame 110 via a vibration damping member 165. The vibration damping member 165 is interposed between the force sensor 61 and the vibration generating source 67, absorbs vibration generated from the vibration generating source 67, and suppresses the transmission of the vibration to the force sensor 61. In the present embodiment, the vibration damping member 165 is a sheet member that is disposed between the master frame 110 and the support portion 109, and suppresses the transmission of vibration of the support portion 109 to which the vibration generating source 67 is attached to the master frame 110, thereby making it more difficult to transmit the vibration of the vibration generating source 67 to the force sensor 61 via the master frame 110, the housing 101, and the like. The vibration damping member 165 is disposed between the support portion 109 and the master frame 110, thereby making it possible to transmit vibration generated by the vibration generating source 67 to the contact portion 105 without going through the vibration damping member 165.

The sheet vibration damping member 165 may include, for example, at least one of carbon fiber reinforced resin, rubber, foam sponge, foam synthetic resin, or gel. These high attenuation rate materials can effectively reduce the transmission rate of vibration from the support portion 109 to the master frame 110. Among them, in the case where the sheet vibration damping member 165 including carbon fiber reinforced resin is used, it is possible to not only lower the transmission rate of vibration, but obtain high rigidity.

In addition, the elastic portion 193 of the support portion 109 has the function of a vibration frequency band limiting portion. In the present embodiment, the elastic portion 193 is a substantially U-shaped portion that connects the frame connection portion 191 to the fixation portion 194, and includes a first elastic portion 193*a* and a second elastic portion 193*b* provided at the center across an opening 192. The elastic portion 193 has an appropriate elastic constant, and performs the function of a low-pass filter that limits the transmission of vibration exceeding a predetermined frequency. Thus, it is possible to selectively adjust a vibration band in accordance with a dynamic range necessary for the force sensor 61.

For example, the elastic constant of the elastic portion 193 can be set at a desired value by adjusting at least one of the Young's modulus of a material included in the elastic portion 193, the thickness, size or shape of the first elastic portion 193*a* and the second elastic portion 193*b*, or the size of the opening 192. For example, force detected by the force sensor 61 corresponds to vibration of a relatively low frequency band, so that the elastic constant of the elastic portion 193 may be set such that the transmission of vibration of a frequency exceeding the frequency band is limited. This makes it possible to suppress the transmission of vibration of a high frequency to the force sensor 61 via the master frame 110, the housing 101, and the like to decrease accuracy in drive control over a slave apparatus and presentation of haptic sensation to a surgeon.

In the present embodiment, the vibration damping member 165 and the elastic portion 193 serving as a vibration frequency band limiting portion are provided between the force sensor 61 and the vibration generating source 67 in the vicinity of the position at which the vibration generating source 67 is attached. That is, the vibration transmission suppressing structure is provided near the contact portion 105 on which an index finger and the like are put in order to pivot the master frame 110. Therefore, the vibration transmission suppressing structure does not limit the transmission of vibration between a part in which force for displacing the position and direction of the operation portion 100 is input from a hand grasping the operation portion 100, and the force sensor 61. Thus, transmission to the force sensor 61 is possible without attenuating the force for displacing the position and direction of the operation portion 100. In contrast, the vibration transmission suppressing structure is not interposed between the vibration generating source 67 and the contact portion 105, so that it is possible to reduce effects on the presentation of tactile sensation to a surgeon.

Figure 17:
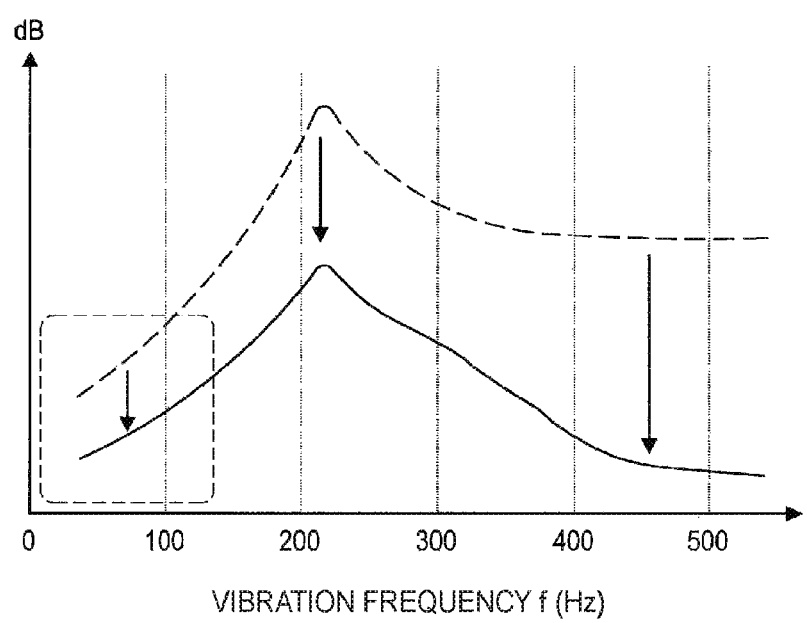
FIG. 17 is an explanatory diagram illustrating magnitude of vibration transmitted to a force sensor for each frequency.

FIG. 17 is a diagram for describing vibration transmission suppressing effects attained by the vibration transmission suppressing structure. The dashed line in FIG. 17 represents vibration that can be generated by the vibration generating source 67 and the magnitude thereof. In addition, the solid line in FIG. 17 represents vibration attenuated by the vibration damping member 165 and the magnitude thereof.

As illustrated in FIG. 17, when tactile sensation is presented to a surgeon, vibration generated by the vibration generating source 67 has a peak, for example, in bands of 210 to 220 Hz, and vibration of a frequency higher than the band of the peak appears on a larger scale than that of vibration of a frequency lower than the band of the peak. The vibration generated by the vibration generating source 67 is attenuated by the vibration damping member 165. In the example illustrated in FIG. 17, vibration of a band of a higher frequency is attenuated relatively more.

In addition, a dynamic range necessary for the force sensor 61, or the vibration frequency of force imparted to the operation portion 100 by a surgeon operating the master apparatus 60 is, for example, less than or equal to 130 Hz in many cases. In this case, the elastic portion 193 serving as a vibration frequency band limiting portion suppresses the transmission of vibration of a frequency exceeding 130 Hz, thereby making it more difficult to transmit vibration of a frequency band other than the frequency band surrounded by the dashed line to the force sensor 61. That is, while the vibration of the frequency band surrounded by the dashed line in FIG. 17 can be transmitted to the force sensor 61 side, vibration of the other frequency bands is made more difficult to transmit to the force sensor 61 side. This makes it possible to accurately execute drive control over a slave apparatus with information detected by the force sensor 61, and control for presenting haptic sensation to a surgeon.

In this way, the master apparatus 60 according to the present embodiment includes the vibration damping member 165 in the operation portion 100, and can hereby suppress the transmission of vibration generated by the vibration generating source 67 for presenting tactile sensation to a surgeon to the force sensor 61. In addition, the master apparatus 60 includes the elastic portion 193 serving as a vibration frequency band limiting portion in the operation portion 100, and can hereby suppress the transmission of vibration other than that of the dynamic range necessary for the force sensor 61. Therefore, vibration noise to the force sensor 61 which is caused by the vibration of the vibration generating source 67 is reduced, and the signal-to-noise ratio (SN ratio) of the force sensor 61 is improved. This makes it possible to increase the sensitivity of the force sensor 61.

3-3. Modification Examples

The configuration example of the operation portion 100 of the master apparatus 60 according to the present embodiment has been described so far. The configuration of the vibration transmission suppressing structure provided to the operation portion 100 is not limited to the example of the embodiment described above. The following describes some modification examples of the vibration transmission suppressing structure.

3-3-1. First Modification Example

Figure 18:
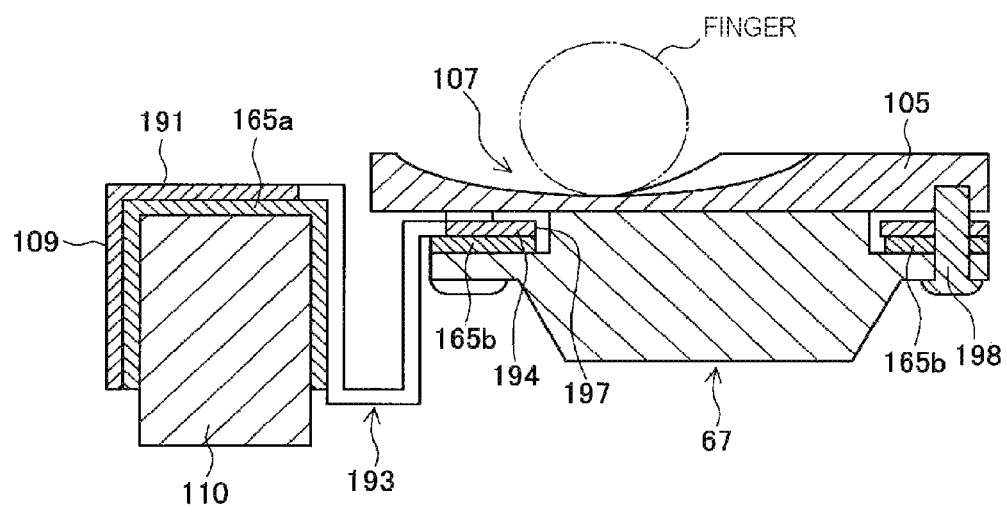
FIG. 18 is a cross-sectional view illustrating a first modification example of the vibration transmission suppressing structure.

FIG. 18 is an explanatory diagram illustrating a vibration transmission suppressing structure according to a first modification example. FIG. 18 is a diagram corresponding to the cross-sectional view of FIG. 15, and corresponds to the schematic diagram of the I-I cross section of FIG. 14. The vibration transmission suppressing structure according to the first modification example is configured such that, when the contact portion 105 and the vibration generating source 67 are fixed to the fixation portion 194 of the support portion 109, the contact portion 105 and the vibration generating source 67 do not directly abut on the fixation portion 194.

Specifically, in the first modification example, a first vibration damping member 165a is disposed between the frame connection portion 191 of the support portion 109 and the master frame 110 similarly to the vibration transmission suppressing structure according to the embodiment described above. In addition, the support portion 109 is provided with the elastic portion 193 serving as a vibration frequency band limiting portion similarly to the vibration transmission suppressing structure according to the embodiment described above. In the first modification example, a second vibration damping member 165b is disposed between the vibration generating source 67 and the fixation portion 194 fixed with a fixing screw 198. Further, there is provided a gap between the contact portion 105 and the fixation portion 194 such that the contact portion 105 and the fixation portion 194 fixed with the fixing screw 198 do not come into direct contact.

Thus, vibration generated by the vibration generating source 67 is made more difficult to transmit the support portion 109 directly or via the contact portion 105, and it is possible to further enhance the effects of suppressing the transmission of the vibration to the master frame 110. This suppresses the transmission of vibration generated by the vibration generating source 67 to the force sensor 61 via the master frame 110, the housing 101 and the like, and it is possible to further increase the sensitivity of the force sensor 61.

Note that a vibration damping member may also be disposed between the contact portion 105 and the fixation portion 194 in the first modification example. In addition, in the first modification example, the first vibration damping member 165a may be omitted in exchange for providing the second vibration damping member 165b.

3-3-2. Second Modification Example

Figure 19:
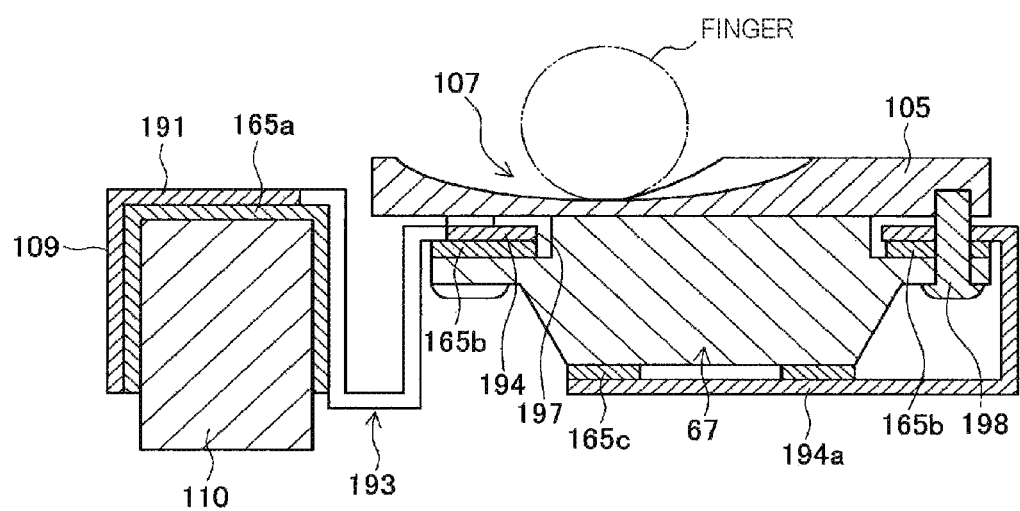
FIG. 19 is a cross-sectional view illustrating a second modification example of the vibration transmission suppressing structure.

FIG. 19 is an explanatory diagram illustrating a vibration transmission suppressing structure according to a second modification example. FIG. 19 is a diagram corresponding to the cross-sectional view of FIG. 15, and corresponds to the schematic diagram of the I-I cross section of FIG. 14. In the vibration transmission suppressing structure according to the second modification example, the vibration generating source 67 is vertically sandwiched by the support portion 109.

Specifically, in the second modification example, a first vibration damping member 165a is disposed between the frame connection portion 191 of the support portion 109 and the master frame 110 similarly to the vibration transmission suppressing structure according to the embodiment described above. In addition, the support portion 109 is provided with the elastic portion 193 serving as a vibration frequency band limiting portion similarly to the vibration transmission suppressing structure according to the embodiment described above. In the second modification example, the fixation portion 194 of the support portion 109 is folded back like the letter U to form a folded-back portion 194a.

The vibration generating source 67 is placed on the folded-back portion 194a, and fixed to the fixation portion 194 with the fixing screw 198.

At this time, the second vibration damping member 165b is disposed between the vibration generating source 67 and the fixation portion 194, and a third vibration damping member 165c is disposed between the vibration generating source 67 and the folded-back portion 194a. In addition, there is provided a gap between the contact portion 105 and the fixation portion 194 such that the contact portion 105 and the fixation portion 194 fixed with the fixing screw 198 do not come into direct contact.

In the vibration transmission suppressing structure according to the second modification example, vibration generated by the vibration generating source 67 is made more difficult to transmit to the support portion 109 directly or via the contact portion 105 even in the case where the support portion 109 is configured to vertically sandwich the vibration generating source 67. Thus, the effects of suppressing the transmission of the vibration to the master frame 110 can be further enhanced. This suppresses the transmission of vibration generated by the vibration generating source 67 to the force sensor 61 via the master frame 110, the housing 101 and the like, and it is possible to further increase the sensitivity of the force sensor 61.

Note that a vibration damping member may also be disposed between the contact portion 105 and the fixation portion 194 in the second modification example. In addition, in the second modification example, the first vibration damping member 165a may be omitted instead of providing the second vibration damping member 165b and the third vibration damping member 165c.

3-3-3. Third Modification Example

Figure 20:
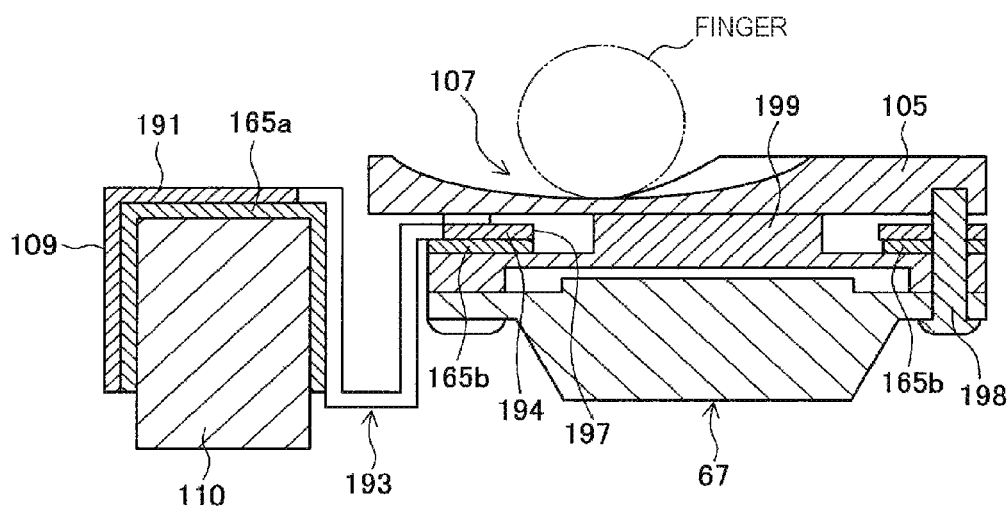
FIG. 20 is a cross-sectional view illustrating a third modification example of the vibration transmission suppressing structure.
Figure 21:
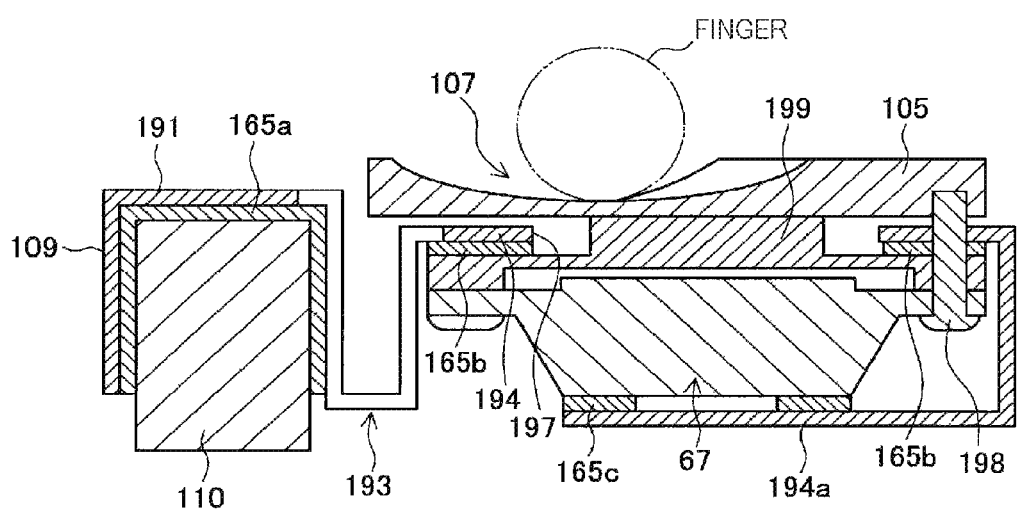
FIG. 21 is a cross-sectional view illustrating the third modification example of the vibration transmission suppressing structure.

FIGS. 20 and 21 are explanatory diagrams illustrating a vibration transmission suppressing structure according to a third modification example. FIGS. 20 and 21 are diagrams each corresponding to the cross-sectional view of FIG. 15, and correspond to the schematic diagram of the I-I cross section of FIG. 14. The vibration transmission suppressing structure according to the third modification example is provided with an intermediate part 199 between the vibration generating source 67 and the fixation portion 194. The example illustrated in FIG. 20 is an example in which the third modification example is applied to the first modification example, and the example illustrated in FIG. 21 is an example in which the third modification example is applied to the second modification example.

Specifically, in the third modification example, the intermediate part 199 is provided between the top of the vibration generating source 67 and the bottom of the fixation portion 194. The intermediate part 199 is fixed to the fixation portion 194 with the fixing screw 198 along with the vibration generating source 67 and the second vibration damping member 165b. The central portion of intermediate part 199 is inserted through a large hole 197 provided to the fixation portion 194 to come into contact with the contact portion 105. In addition, the bottom of the intermediate part 199 comes into contact with the vibration generating source 67 to transmit vibration generated by the vibration generating source 67 to the contact portion 105. The second vibration damping member 165b is disposed between the intermediate part 199 and the bottom of the fixation portion 194. In addition, there is provided a gap between the contact portion 105 and the fixation portion 194.

The transmission of vibration from the intermediate part 199 to the fixation portion 194 is suppressed.

In the vibration transmission suppressing structure according to the third modification example, even in the case where the intermediate part 199 is provided between the top of the vibration generating source 67 and the fixation portion 194, vibration generated by the vibration generating source 67 is made more difficult to transmit to the support portion 109 via the intermediate part 199 or the contact portion 105. Thus, the effects of suppressing the transmission of the vibration to the master frame 110 can be further enhanced. This suppresses the transmission of vibration generated by the vibration generating source 67 to the force sensor 61 via the master frame 110, the housing 101 and the like, and it is possible to further increase the sensitivity of the force sensor 61.

Note that a vibration damping member may also be disposed between the contact portion 105 and the fixation portion 194 in the third modification example. In addition, in the third modification example, the first vibration damping member 165a may be omitted instead of providing the second vibration damping member 165b and the third vibration damping member 165c.

3-3-4. Fourth Modification Example

Figure 22:
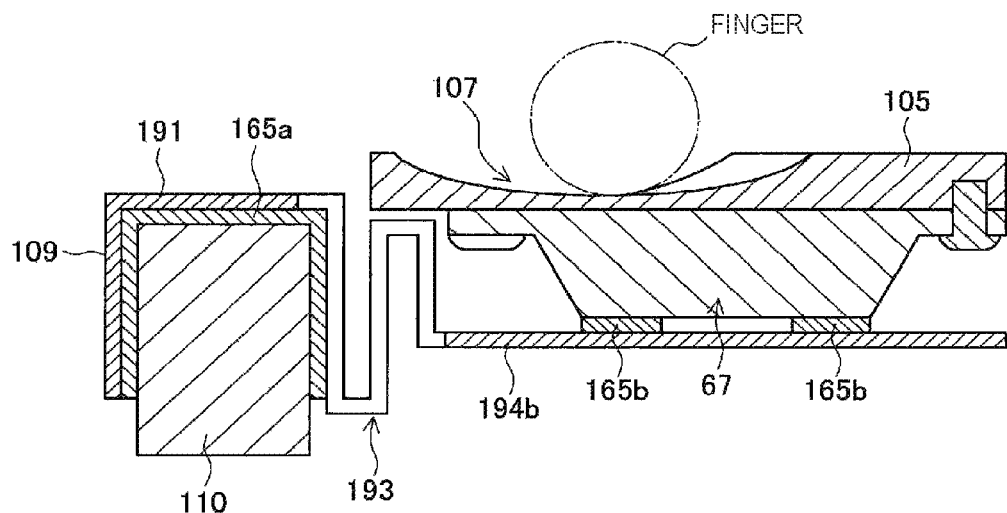
FIG. 22 is a cross-sectional view illustrating a fourth modification example of the vibration transmission suppressing structure.

FIG. 22 is an explanatory diagram illustrating a vibration transmission suppressing structure according to a fourth modification example. FIG. 22 is a diagram corresponding to the cross-sectional view of FIG. 15, and corresponds to the schematic diagram of the I-I cross section of FIG. 14. In the vibration transmission suppressing structure according to the fourth modification example, the vibration generating source 67 and the contact portion 105 are fixed onto the top of a fixation portion 194b of the support portion 109.

Specifically, in the fourth modification example, a first vibration damping member 165a is disposed between the frame connection portion 191 of the support portion 109 and the master frame 110 similarly to the vibration transmission suppressing structure according to the embodiment described above. In addition, the support portion 109 is provided with the elastic portion 193 serving as a vibration frequency band limiting portion similarly to the vibration transmission suppressing structure according to the embodiment described above. In the fourth modification example, the vibration generating source 67 and the contact portion 105 are integrally configured. The integrated vibration generating source 67 and contact portion 105 are attached onto the fixation portion 194b of the support portion 109. A method for fixing the vibration generating source 67 to the fixation portion 194b is not limited in particular. The vibration generating source 67 is attached onto the top of the fixation portion 194b, so that the position of the fixation portion 194b is lower as compared with the case of the vibration transmission suppressing structure according to the embodiment described above. In the example illustrated in FIG. 22, the elastic portion 193 serving as a vibration frequency band limiting portion is shaped like not the letter U, but the letter S, thereby lowering the position of the fixation portion 194b.

The second vibration damping member 165b is disposed between the vibration generating source 67 and the fixation portion 194b. In addition, there is also provided a gap not to bring the contact portion 105 into direct contact with the support portion 109. Thus, vibration generated by the vibration generating source 67 is made more difficult to transmit the support portion 109 directly or via the contact portion 105, and it is possible to further enhance the effects of suppressing the transmission of the vibration to the master frame 110. This suppresses the transmission of vibration generated by the vibration generating source 67 to the force sensor 61 via the master frame 110, the housing 101 and the like, and it is possible to further increase the sensitivity of the force sensor 61.

Note that, in the fourth modification example, the first vibration damping member 165a may be omitted instead of providing the second vibration damping member 165b.

3-3-5. Fifth Modification Example

Figure 23:
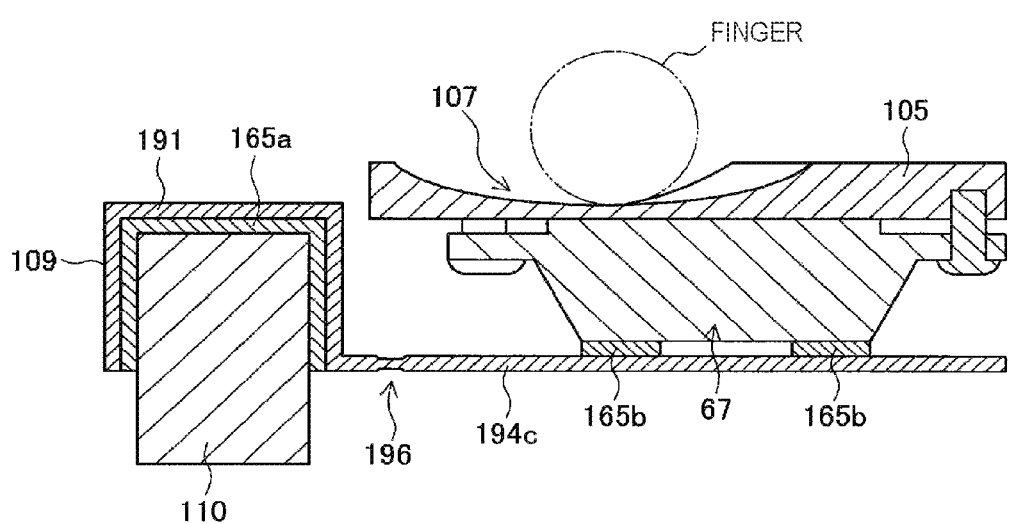
FIG. 23 is a cross-sectional view illustrating a fifth modification example of the vibration transmission suppressing structure.

FIG. 23 is an explanatory diagram illustrating a vibration transmission suppressing structure according to a fifth modification example. FIG. 23 is a diagram corresponding to the cross-sectional view of FIG. 15, and corresponds to the schematic diagram of the I-I cross section of FIG. 14. In the vibration transmission suppressing structure according to the fifth modification example, the configuration of a vibration frequency band limiting portion is different from that of the case of the vibration transmission suppressing structure according to the embodiment described above.

Specifically, in the fifth modification example, a first vibration damping member 165a is disposed between the frame connection portion 191 of the support portion 109 and the master frame 110 similarly to the vibration transmission suppressing structure according to the embodiment described above. In addition, in the fifth modification example, the vibration generating source 67 and the contact portion 105 are integrally configured, and attached onto a fixation portion 194c of the support portion 109 cantilevered by the master frame 110. The second vibration damping member 165b is disposed between the vibration generating source 67 and the fixation portion 194c.

In the fifth modification example, there is provided a thin portion 196 that is thinned on the proximal end side of a fixation portion 194c provided from the frame connection portion 191 of the support portion 109 in a linked manner. The rigidity of the thin portion 196 is smaller than that of the other parts, so that the thin portion 196 has elasticity. The thin portion 196 functions as a vibration frequency band limiting portion that limits the frequency band of vibration transmitted from the vibration generating source 67 to the master frame 110 side. The thin portion 196 has an appropriate elastic constant, and performs the function of a low-pass filter that limits the transmission of vibration exceeding a predetermined frequency. Thus, it is possible to selectively adjust a vibration band in accordance with a dynamic range necessary for the force sensor 61.

For example, the elastic constant of the thin portion 196 can be set at a desired value by adjusting at least one of the Young's modulus of a material included in the thin portion 196, or the thickness, size, disposition position or shape of the thin portion 196. Even in the case of the use of the thin portion 196, it is possible to suppress the transmission of vibration of a high frequency to the force sensor 61 via the master frame 110, the housing 101, and the like to decrease accuracy in drive control over a slave apparatus and presentation of haptic sensation to a surgeon. This suppresses the transmission of vibration generated by the vibration generating source 67 as vibration noise to the force sensor 61, and it is possible to further increase the sensitivity of the force sensor 61.

Note that, in the fifth modification example, the first vibration damping member 165a may be omitted instead of providing the second vibration damping member 165b.

3-3-6. Sixth Modification Example

Figure 24:
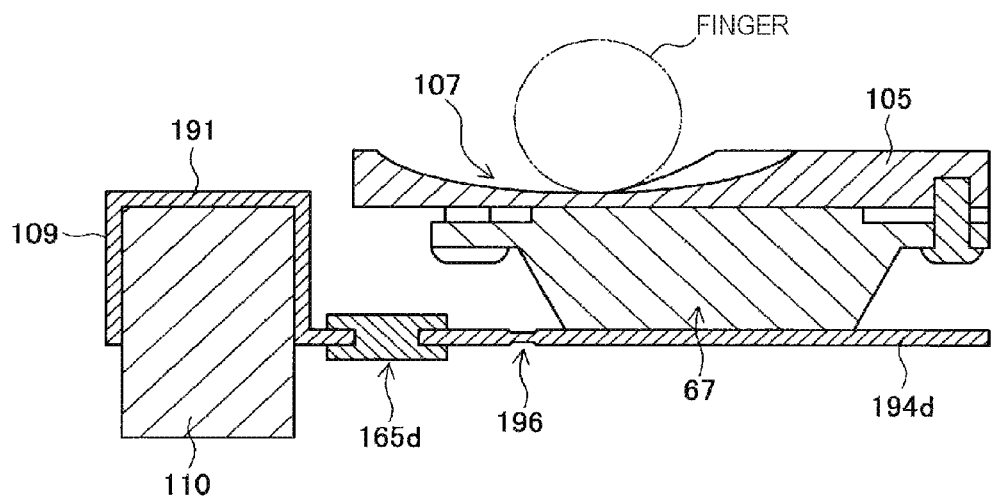
FIG. 24 is a cross-sectional view illustrating a sixth modification example of the vibration transmission suppressing structure.

FIG. 24 is an explanatory diagram illustrating a vibration transmission suppressing structure according to a sixth modification example. FIG. 24 is a diagram corresponding to the cross-sectional view of FIG. 15, and corresponds to the schematic diagram of the I-I cross section of FIG. 14. In the vibration transmission suppressing structure according to the sixth modification example, the way in which a vibration damping member is attached is different from that of the case of the vibration transmission suppressing structure according to the embodiment described above. The example illustrated in FIG. 24 is an example in which the sixth modification example is applied to the fifth modification example.

Specifically, while the vibration damping member is a sheet member disposed between the frame connection portion 191 and the master frame 110, or between the vibration generating source 67 and the fixation portion 194 in the embodiment and each modification example described above, a vibration damping member 165d is configured as a member that connects the frame connection portion 191 of the support portion 109 to a fixation portion 194d in the sixth modification example. That is, in the vibration transmission suppressing structure according to the sixth modification example, the support portion 109 is configured by coupling the part of the frame connection portion 191 side which includes, for example, stainless steel to the part of the fixation portion 194d side via the vibration damping member 165d.

For example, the vibration generating source 67 integrated with the contact portion 105 is directly attached onto the fixation portion 194d. In addition, the proximal end side of the fixation portion 194d is provided with the thin portion 196 serving as a vibration frequency band limiting portion. The vibration damping member 165d has, for example, an H-shaped cross section, and the respective end portions are fixed to the part of the frame connection portion 191 side and the part of the fixation portion 194d side. The vibration damping member 165d according to the sixth modification example may also include, for example, at least one of carbon fiber reinforced resin, rubber, foam sponge, foam synthetic resin, or gel.

The vibration damping member 165d attenuates vibration generated by the vibration generating source 67 to make the vibration more difficult to transmit to the master frame 110. In addition, the thin portion 196 limits the frequency band of vibration transmitted from the vibration generating source 67 to the master frame 110 side. This suppresses the transmission of vibration generated by the vibration generating source 67 as vibration noise to the force sensor 61, and it is possible to further increase the sensitivity of the force sensor 61.

Note that, in the sixth modification example, in addition to the vibration damping member 165d, there may be provided a vibration damping member in at least one of the areas between the frame connection portion 191 of the support portion 109 and the master frame 110, or between the fixation portion 194d and the vibration generating source 67.

3-3-7. Seventh Modification Example

Figure 25:
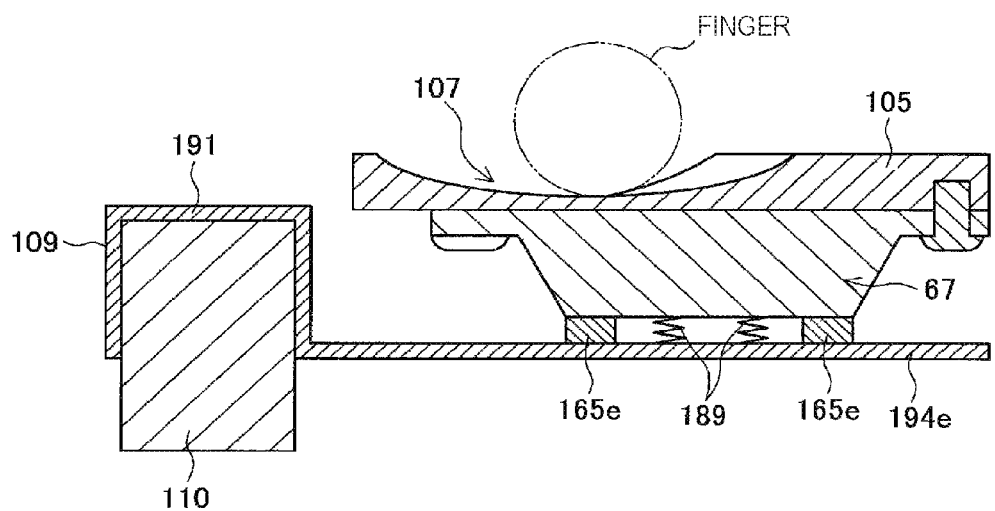
FIG. 25 is a cross-sectional view illustrating a seventh modification example of the vibration transmission suppressing structure.

FIG. 25 is an explanatory diagram illustrating a vibration transmission suppressing structure according to a seventh modification example. FIG. 25 is a diagram corresponding to the cross-sectional view of FIG. 15, and corresponds to the schematic diagram of the I-I cross section of FIG. 14. The vibration transmission suppressing structure according to the seventh modification example is an example in which a coil spring is used to configure a vibration frequency band limiting portion.

Specifically, in the seventh modification example, the support portion 109 includes the frame connection portion 191 and a fixation portion 194e. The frame connection portion 191 is mounted on the master frame 110, and the fixation portion 194e extends in the direction away from the master frame 110. The support portion 109 is cantilevered by the master frame 110. In the example illustrated in FIG. 25, the vibration generating source 67 integrated with the contact portion 105 is attached onto the fixation portion 194e. In the fifth modification example, a vibration damping member 165e and a coil spring 189 are disposed between the vibration generating source 67 and the fixation portion 194e. In the example illustrated in FIG. 25, the two coil springs 189 support the vibration generating source 67 on the fixation portion 194e, and the vibration damping member 165e is disposed to surround the two coil springs 189.

Vibration generated by the vibration generating source 67 can be attenuated by the vibration damping member 165e, and transmitted to the fixation portion 194e. In addition, the coil spring 189 provided between the vibration generating source 67 and the fixation portion 194e functions as a vibration frequency band limiting portion. The coil spring 189 has an appropriate elastic constant, and performs the function of a low-pass filter that limits the transmission of vibration exceeding a predetermined frequency. Thus, it is possible to selectively adjust a vibration band in accordance with a dynamic range necessary for the force sensor 61. This suppresses the transmission of vibration generated by the vibration generating source 67 as vibration noise to the force sensor 61, and it is possible to further increase the sensitivity of the force sensor 61.

Note that, in the seventh modification example, the disposition position and form of the coil spring 189 are not limited to the example described above. The vibration frequency band limiting portion may include a spring structure other than the coil spring 189. In addition, the disposition position and form of the vibration damping member 165e are not also limited to the example described above. Further, in the seventh modification example, in addition to the vibration damping member 165e, there may be provided a vibration damping member between the frame connection portion 191 of the support portion 109 and the master frame 110.

4. Conclusion

As described above, the master apparatus 60 serving as a haptic presentation apparatus according to the present embodiment includes the vibration damping member 165 that is interposed between the force sensor 61 and the vibration generating source 67. Therefore, vibration generated by the vibration generating source 67 is attenuated and transmitted to the force sensor 61 side. Thus, it is possible to suppress the transmission of vibration noise by the vibration generating source 67 which is not force input by a surgeon to the operation portion 100 which is a target of detection of the force sensor 61 to the force sensor 61.

In addition, the master apparatus 60 according to the present embodiment includes a vibration frequency band limiting portion that is interposed between the force sensor 61 and the vibration generating source 67. Therefore, the transmission of vibration of a frequency of a frequency band other than a predetermined frequency band from the vibration generating source 67 to the force sensor 61 side is suppressed. Thus, it is possible to suppress the transmission of vibration of a frequency band other than the frequency band corresponding to the dynamic range of the force sensor 61 from the vibration generating source 67 to the force sensor 61.

In this way, the transmission of vibration generated by the vibration generating source 67 as vibration noise to the force sensor 61 is suppressed, and the master apparatus 60 according to the present embodiment can increase the sensitivity of the force sensor 61. Thus, it is possible to accurately present haptic sensation to a surgeon in a haptic presentation apparatus that has a function of presenting tactile sensation.

In addition, the master apparatus 60 according to the present embodiment can adjust the balance between the strength of vibration for presenting tactile sensation and the degree to which vibration noise to the force sensor 61 is reduced by adjusting at least one of the hardness, rigidity, Young's moduli or elastic constants of the vibration damping member 165 and the vibration frequency band limiting portion in accordance with the frequency characteristics of the force sensor 61 and the frequency characteristics of the vibration generating source 67. Thus, it is possible to present tactile sensation and present haptic sensation to a surgeon in a balanced manner in a haptic presentation apparatus that has a function of presenting tactile sensation.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure. In addition, it should be understood that the combination of the embodiment described above with each modification example described above naturally comes under the technical scope of the present disclosure.

For example, the embodiment described above adopts the configuration in which vibration generated by the vibration generating source 67 is transmitted to a finger of a surgeon via the contact portion 105 in contact with the vibration generating source 67, but the present disclosure is not limited to the example. For example, the configuration may be adopted in which the contact portion 105 is omitted, and a finger of a surgeon comes into direct contact with the vibration generating source 67.

In addition, a vibration frequency band limiting portion is implemented by using a member having a predetermined elastic constant in the embodiment described above, but the present disclosure is not limited to the example. For example, when generating a driving signal for the vibration generating source 67, the first vibration transmission portion 70 may limit the frequency band of vibration to be transmitted to the force sensor 61 by using signal processing to shape the driving signal in advance.

In addition, the embodiment described above has been described by using a grasping haptic presentation apparatus including a writing pen type operation portion 100 as an example, but the present disclosure is not limited thereto. For example, the haptic presentation apparatus may be a grasping haptic presentation apparatus like scissors. In addition, the haptic presentation apparatus is not limited to an apparatus applicable to a medical robot system, but may be applied to a variety of apparatuses such as industrial products and hobby products.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A haptic presentation apparatus including:

a force sensor configured to detect force input to an operation portion that is operated by a user;

a vibration generating source configured to present tactile sensation to the user; and a vibration damping member configured to be interposed between the force sensor and the vibration generating source.

(2)

The haptic presentation apparatus according to (1), in which the operation portion includes a contact portion that comes into contact with a part of the user, the vibration generating source is provided in a vicinity of the contact portion, and the vibration damping member is interposed between the force sensor and the vibration generating source in the vicinity of the contact portion.

(3)

The haptic presentation apparatus according to (2), in which the operation portion is a grasping device including a movable portion that is displaced upon receiving force input by the user, and includes the contact portion in the movable portion, the contact portion coming into contact with a finger of the user, and the vibration damping member is provided to the movable portion.

(4)

The haptic presentation apparatus according to (2) or (3), in which the operation portion includes a frame portion, and the contact portion is provided to a support portion that is cantilevered by the frame portion, and the vibration damping member is interposed between the frame portion and the support portion.

(5)

The haptic presentation apparatus according to any one of (2) to (4), in which vibration generated by the vibration generating source is transmitted to the contact portion without going through the vibration damping member.

(6)

The haptic presentation apparatus according to any one of (1) to (5), in which the vibration damping member includes at least one of carbon fiber reinforced resin, rubber, foam sponge, foam synthetic resin, or gel.

(7)

The haptic presentation apparatus according to any one of (1) to (6), further including:

a vibration frequency band limiting portion configured to be interposed between the force sensor and the vibration generating source.

(8)

The haptic presentation apparatus according to (7), in which the vibration frequency band limiting portion transmits vibration of a band of a frequency less than a predetermined frequency to the force sensor side.

(9)

The haptic presentation apparatus according to (7) or (8), in which the vibration frequency band limiting portion has rigidity corresponding to a band of a vibration frequency transmitted from the vibration generating source side to the force sensor.

(10)

The haptic presentation apparatus according to any one of (7) to (9), in which the vibration frequency band limiting portion includes a spring structure or a hinge structure.

(11)

The haptic presentation apparatus according to any one of (7) to (10), in which the operation portion includes a contact portion that comes into contact with a part of the user, the vibration generating source is provided in a vicinity of the contact portion, and the vibration frequency band limiting portion is interposed between the force sensor and the vibration generating source in the vicinity of the contact portion.

(12)

The haptic presentation apparatus according to (11), in which the operation portion is a grasping device including a movable portion that is displaced upon receiving force input by the user, and includes the contact portion in the movable portion, the contact portion coming into contact with a finger of the user, and the vibration frequency band limiting portion is provided to the movable portion.

(13)

The haptic presentation apparatus according to (11) or (12), in which the operation portion includes a frame portion, and the contact portion is provided to a support portion that is cantilevered by the frame portion, and the vibration frequency band limiting portion includes an elastic structure provided to a cantilevering structure.

(14)

The haptic presentation apparatus according to any one of (1) to (13), in which the haptic presentation apparatus is a master side device of a master slave apparatus.

(15)

The haptic presentation apparatus according to (14), in which the haptic presentation apparatus is an input apparatus for remotely operating a medical instrument.

REFERENCE SIGNS LIST 1 medical robot system
60 master apparatus (haptic presentation apparatus)
61 force sensor
65 motor
67 vibration generating source
79 control apparatus
100 operation portion
105 contact portion
109 support portion 110 master frame
165 vibration damping member
191 frame connection portion
193 elastic portion (vibration frequency band limiting portion)
194 fixation portion

The invention claimed is:

1. A haptic presentation apparatus comprising:
a force sensor configured to detect force input to an operation portion that is operated by a user, and generate an electric signal corresponding to the detected force input;
a vibration actuator configured to present tactile sensation to the user;
a vibration damping sheet configured to be interposed between the force sensor and the vibration actuator;
a first mechanical part contacting the force sensor; and
a second mechanical part contacting the vibration actuator, wherein the vibration damping sheet is provided between the first mechanical part and the second mechanical part, such that the vibration damping sheet contact neither the force sensor nor the vibration actuator,
wherein the operation portion includes a contact portion that comes into contact with a part of the user,
the vibration actuator is provided adjacent to the contact portion, and
the vibration damping sheet is interposed between the force sensor and the vibration actuator adjacent to the contact portion,
wherein the operation portion is a grasping interface including a movable portion that is displaced upon receiving the force input by the user, and includes the contact portion in the movable portion, the contact portion coming into the contact with a finger of the user, and
the vibration damping sheet is provided to the movable portion.

2. The haptic presentation apparatus according to claim 1, wherein
the operation portion includes a frame portion, and the contact portion is provided to a support portion that is cantilevered by the frame portion, and
the vibration damping sheet is interposed between the frame portion and the support portion.

3. The haptic presentation apparatus according to claim 1, wherein
vibration generated by the vibration actuator is transmitted to the contact portion without going through the vibration damping sheet.

4. The haptic presentation apparatus according to claim 1, wherein
the vibration damping sheet includes at least one of carbon fiber reinforced resin, rubber, foam sponge, foam synthetic resin, or gel.

5. The haptic presentation apparatus according to claim 1, further comprising:
a vibration frequency band suppressor configured to be interposed between the force sensor and the vibration actuator.

6. The haptic presentation apparatus according to claim 5, wherein
the vibration frequency band suppressor transmits vibration of a band of a frequency less than a predetermined frequency to the force sensor.

7. The haptic presentation apparatus according to claim 5, wherein
the vibration frequency band suppressor has elasticity or rigidity corresponding to a band of a vibration frequency transmitted from the vibration actuator to the force sensor.

8. The haptic presentation apparatus according to claim 5, wherein
the vibration frequency band suppressor includes an elastic structure or a spring structure.

9. The haptic presentation apparatus according to claim 5, wherein
the operation portion includes the contact portion that comes into the contact with the part of the user,
the vibration actuator is provided adjacent to the contact portion, and
the vibration frequency band suppressor is interposed between the force sensor and the vibration actuator adjacent to the contact portion.

10. The haptic presentation apparatus according to claim 9, wherein the operation portion is the grasping interface including the movable portion that is displaced upon said receiving the force input by the user, and includes the contact portion in the movable portion, the contact portion coming into the contact with the finger of the user, and the vibration frequency band suppressor is provided to the movable portion.

11. The haptic presentation apparatus according to claim 9, wherein
the operation portion includes a frame portion, and the contact portion is provided to a support portion that is cantilevered by the frame portion, and
the vibration frequency band suppressor includes an elastic structure provided to a cantilevering structure.

12. The haptic presentation apparatus according to claim 1, wherein the haptic presentation apparatus is a master side apparatus of a master slave apparatus.

13. The haptic presentation apparatus according to claim 12, wherein the haptic presentation apparatus is an input apparatus for remotely operating a medical instrument.

14. The haptic presentation apparatus according to claim 1, wherein
the first mechanical part comprises a plurality of first mechanical parts, and the second mechanical part comprises a plurality of second mechanical parts.

15. The haptic presentation apparatus according to claim 1, wherein
the first mechanical part comprises a first arm, a second arm, and a joint portion joining the first arm and the second arm.

16. The haptic presentation apparatus according to claim 1, wherein
the second mechanical part comprises a support portion supporting the operation portion.

17. The haptic presentation apparatus according to claim 1, wherein
a distance between the vibration actuator and the vibration damping sheet is shorter than a distance between the force sensor and the vibration damping sheet.

* * * * *